US008609732B2

(12) United States Patent
Gillet et al.

(10) Patent No.: US 8,609,732 B2
(45) Date of Patent: Dec. 17, 2013

(54) INHIBITORS OF THE SHIGA TOXINS TRAFFICKING THROUGH THE RETROGRADE PATHWAY

(75) Inventors: Daniel Gillet, Paris (FR); Julien Barbier, Gif-sur-Yvette (FR); Ludger Johannes, Courbevoie (FR); Bahne Stechmann, Hattstedt (DE); Siau-Kun Bai, Villeneuve Saint-Georges (FR)

(73) Assignees: Commissariat a l'Energie Atomique et aux Energies Alternatives, Paris (FR); Institut Curie, Paris (FR); Centre National de la Recherche Scientfique, Paris (FR)

( * ) Notice: Subject to any disclaimer, the term of this patent is extended or adjusted under 35 U.S.C. 154(b) by 187 days.

(21) Appl. No.: 12/999,749

(22) PCT Filed: Jun. 17, 2009

(86) PCT No.: PCT/IB2009/006334

§ 371 (c)(1),
(2), (4) Date: Mar. 23, 2011

(87) PCT Pub. No.: WO2009/153665

PCT Pub. Date: Dec. 23, 2009

(65) Prior Publication Data

US 2011/0201601 A1 Aug. 18, 2011

(30) Foreign Application Priority Data

Jun. 17, 2008 (EP) .................................... 08290570

(51) Int. Cl.
*A61K 31/65* (2006.01)

(52) U.S. Cl.
USPC ............ 514/619; 514/415; 514/438; 514/461

(58) Field of Classification Search
USPC .................................. 514/415, 438, 461, 619
See application file for complete search history.

(56) References Cited

U.S. PATENT DOCUMENTS 6,177,280 B1 1/2001 Yan et al.

FOREIGN PATENT DOCUMENTS

WO 98 28298 7/1998

OTHER PUBLICATIONS

Yongquing et al, Synthetic Comm., 2004, 34(17), 3235-3242.*
RN 143424-08-2, 1992(Abstract only).*
International Search Report issed Feb. 23, 2010 in PCT/IB09/06334 filed Jun. 17, 2009.
Ikeda, Masahiro et al., "Inhibitory effect of tyrphostin 47 on Shiga toxin-induced cell death", European Journal of Pharmacology, vol. 546, No. 1-3, pp. 36-39, XP025169806, ISSN: 0014-2999, (Sep. 28, 2006).
Saenz, B. Jose et al., "Identification and Characterization of Small Molecules That Inhibit Intracellular Toxin Transport", Infection and Immunity, vol. 75, No. 9, pp. 4552-4561, XP002529419, (Sep. 2007).
Decaudin, Didier et al., "Peripheral Benzodiazepine Receptor Ligands Reverse Apoptosis Resistance of Cancer Cells in Vitro and in Vivo". Cancer Research, vol. 62, pp. 1388-1393, XP002558918, (Mar. 1, 2002).

* cited by examiner

*Primary Examiner* — Shailendra Kumar
(74) *Attorney, Agent, or Firm* — Oblon, Spivak, McClelland, Maier & Neustadt, L.L.P.

(57) ABSTRACT

The present invention relates to the use of compounds of general formula (I) and (II) for the preparation of a drug for preventing and/or treating disorders caused by Shiga toxins and related toxins.

4 Claims, 6 Drawing Sheets

INHIBITORS OF THE SHIGA TOXINS TRAFFICKING THROUGH THE RETROGRADE PATHWAY

This application is a 371 of PCT/IB09/06334, filed Jun. 17, 2009.

The invention relates to the use of imine and benzodiazepine derivatives as therapeutic agents, particularly in the treatment of disorders caused by Shiga toxins.

*Shigella dysenteriae*, some strains of *Escherichia coli* as well as other bacteria can secrete Shiga toxins (Stxs), which cause serious complications and deaths during infections.

There are multiple sources of Shiga toxin producing pathogens involved in sporadic cases and outbreaks of disease. Shiga toxin producing bacteria are associated with a broad spectrum of clinical manifestations in humans ranging from asymptomatic colonization to life threatening hemolytic uremic syndrome (HUS) (Tarr et al. (2005). Lancet 365, 1073-1086).

In North America, most cases and outbreaks of infection by these pathogens have been associated with Shiga toxin-producing *Escherichia coli* (STEC) and more specifically the single *E. coli* serotype O157:H7. These endemic or epidemic cases begin through the ingestion of STEC. Although STEC infection may be asymptomatic, it typically begins with an onset of watery diarrhea between 2 and 12 days after STEC ingestion and is frequently associated with abdominal pain and occasionally with nausea and vomiting (Tarr et al., 2005). Watery diarrhea lasts for 1-3 days after which, in 90% of the cases, it progresses to bloody diarrhea (Tarr at al., 2005). Then approximately 15% of the STEC-infected subjects develop HUS.

The course of the disease between bloody or non-bloody diarrhea and HUS is not well characterized but the HUS is defined as microangiopathic hemolytic anemia (with fragmented red blood cells: schistocytes), thrombocytopenia and nephropathy. Other extra-renal complications of HUS may also subsequently occur such as seizures, intracranial infarction or hemorrhage, retinal hemorrhage and encephalopathy, acute pancreatitis, cardiomyopathy and death (in ~4%) (Elliott, E. J., and Robins-Browne, R. M. (2005). Curr Probl Pediatr Adolesc Health Care 35, 310-330). Even though approximately half of STEC infections do not require medical care, a small percentage of cases develop HUS with after-effects such as chronic kidney failure requiring lifelong dialysis or a kidney transplant.

Centers for Disease Control and Prevention (CDC) provides epidemiological figures of the number of incident STEC infections (Mead et al., (1999) Emerg Infect Dis 5, 607-625). Authors evaluated the total number of STEC infections annually to be 110,220 in USA.

Shiga toxins belong to the toxins that use the cell retrograde transport; these toxins include ricin (produced in the seeds of the castor oil plant *Ricinus communis*), Shiga and Shiga-like toxins (Stx1 and Stx2, together designated Stxs, produced by *Shigella dysenteriae* and *E. coli*), cholera toxin (Ctx produced by *Vibrio cholerae*), heat-labile enterotoxin (produced by *E. coli*), pertussis toxin (produced by *Bordetella pertussis*), and subtilase cytotoxin (produced by *E. coli*). These toxins share a similar structural organization: a receptor-binding B-subunit associated with a catalytic active A-subunit.

After binding to their target cell receptors, these toxins are internalized and transported to early endosomes (EE). Instead of being recycled back to the plasma membrane or transported to late endosomes/lysosomes for degradation, an important number of toxin molecules gain access to the Golgi apparatus and the endoplasmic reticulum (ER), from where their A-subunits are retro-translocated into the cytosol (Sandvig et al. (2002) Annu. Rev. Cell Dev. Biol. 18:1-24). Then, the A-subunits of Stxs toxins and ricin remove a conserved adenine-residue from ribosomal RNA, leading to an inhibition of protein biosynthesis and apoptosis, whereas the A-subunit of cholera toxin modifies the stimulatory G-protein $G_s\alpha$, causing the untamed, constitutive production of the secondary messenger cAMP, which finally provokes a dramatic efflux of ions and water from the digestive track.

The unique intracellular transport pathway of these toxins from the early endosomes to the ER via the Golgi apparatus (retrograde transport) offers the opportunity to search for pharmacologically active compounds capable of blocking this pathway. Small molecules that inhibit the retrograde transport of these toxins would prevent their delivery into the cytosol, where they exert their deadly effect.

To date, there is no proven safe treatment for STEC infections and prevention of Shiga toxin-mediated complications other than supportive care. Moreover, the use of antibiotics seems to exacerbate the disease. Considering that Shiga toxin is the major virulence factor secreted by STEC and that Stxs plays a pivotal role in the pathogenesis of HUS, most treatment strategies aim at neutralizing Stxs.

Development of compounds capable of inhibiting the cellular toxin binding targeting the B-subunit of the toxin has been studied leading to a synthetic analog of Shiga toxin receptor, this analog is composed of silicon dioxide particles covalently linked to the trisaccharide moiety (globotriose [α-D-Gal-(1→4)-β-D-Gal-(1→4)-D-Glc]) of the globotriaosylceramide molecule that mediates Shiga toxin binding; it was the first compound that was tested in humans (Synsorb Pk, see Armstrong et al., 1995). Synsorb Pk was designed to trap and eliminate free Stxs produced in the gut of patients infected by Stx-producing *E. coli*, and to prevent the progression of hemorrhagic colitis to hemolytic uremic syndrome. However, this Shiga toxin-binding agent failed to diminish the severity of disease in pediatric patients with diarrhea-associated HUS (Trachtman et al., (2003) Jama 290, 1337-1344).

Since then, other molecules with improved affinity towards the B-subunit of Stxs (StxB) have been developed:

a water-soluble carbohydrate ligand of Stxs, analog to its carbohydrate receptor (Starfish, see Kitov et al. (2000) Nature 403, 669-672):

3

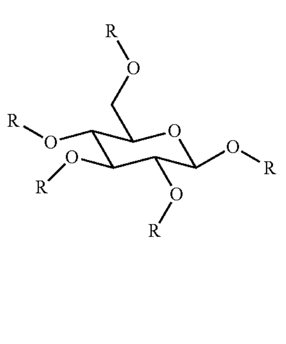

-continued

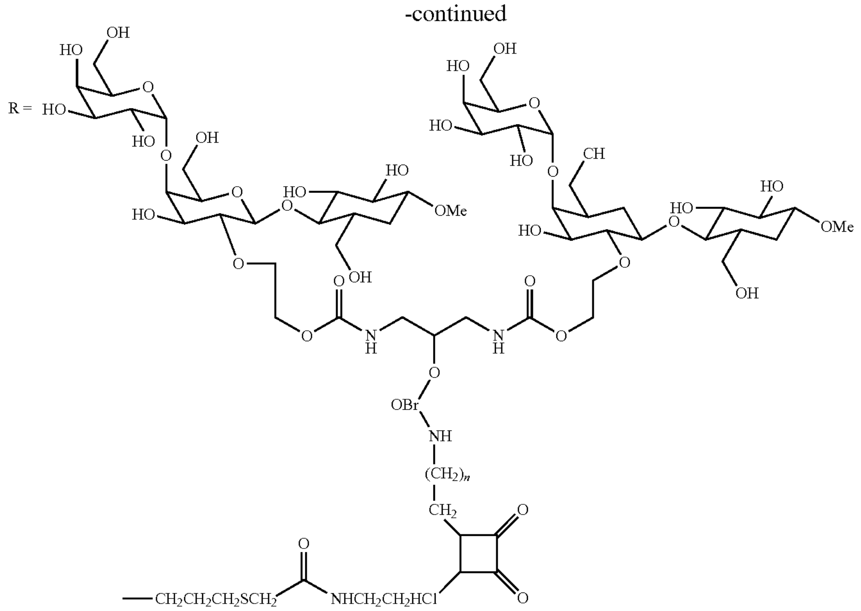

Structure of the Water Soluble Ligand of Stxs, Starfish a carbosilane dendrimer carrying various numbers of trisaccharides which is the first synthetic Stx2 inhibitor to function in vivo (Super Twig, Nishikawa et al. (2002) Proc Natl Acad Sci USA 99, 7669-7674). However, the clinical application of these carbosilane dendrimers has been substantially hampered by the synthetic complexity of its trisaccharide moiety.

SUPER TWIGs (0)3

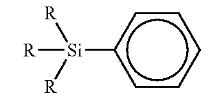

(1)6

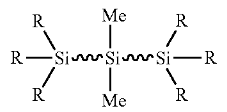

(1)12

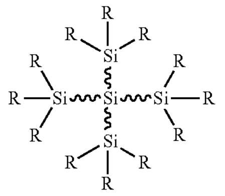

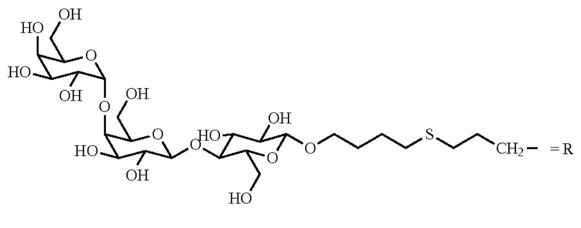

Structure of the Synthetic Stx2 Inhibitor, Super Twig others Stx inhibitors, containing trisaccharides, have also been described for their ability to protect animals.

Another approach aims at inactivating the catalytic active A-subunit of the toxin (StxA).

Several purine derivatives have been assayed as inhibitors of Stx RNA-N-glycosidase activity. 4-aminopyrazolo[3,4-d] pyrimidine (4-APP) is by far the most potent inhibitor of enzymatic reactions catalyzed by Stx1. However, experiments were realized in acellular in vitro assay and the IC50 of Stx1 was shifted by one order of magnitude in presence of 0.8 mM 4-APP. Thus, it appears that therapeutic potential of such compounds is low.

Another strategy intends to act directly on cellular processes hijacked by Stxs and not on the toxin itself. In the past, it has been shown for a limited number of small molecules that they are able to inhibit the retrograde transport of certain toxins (Ricin, Shiga and cholera toxins), Exo2 (Spooner et al. (2008) Biochem J 414, 471-484), Brefeldin A (Donta et al., 1995), Golgicide and others (Saenz et al. (2007) Infect Immun 75, 4552-4561; Saenz et al. (2009) Nat Chem Biol 5, 157-165).

Yet, these compounds are rather unspecific, as they affect the morphology of cellular compartments. Their effect is thus not restricted to the retrograde transport pathway (the anterograde/biosynthetic transport is affected, too) or to these toxins (the transport of endogenous proteins is affected as well). Treatment is most likely not possible without causing severe side effects.

There is thus a need for the development of compounds intended for safe treatment for infections and prevention of Shiga toxin-mediated complications other than supportive care.

The inventors have found that unexpectedly the compounds of formula (I) (imine derivatives) and the compounds of formula (II) (benzodiazepine derivatives) are efficient for preventing and/or treating Shiga toxins cells intoxications.

The present invention relates to the use of an imine derivative of formula (I):

(I)

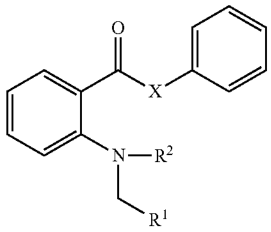

wherein:

X is —NH— or —O—;

$R^1$ is a cycloalkyl radical having 5 to 10 carbon atoms, having one or two rings, saturated or not, wherein one or more carbon atom may be replaced by a nitrogen, oxygen or sulfur atoms; said cycloalkyl radical being optionally substituted by one or more groups chosen amongst a halogen atom, a hydroxyl function, a nitro function and a $C_1$-$C_3$ alkyl group, $R^2$ is a hydrogen atom or a link; when $R^2$ is a link, then the nitrogen atom forms a double bond with the adjacent carbon atom;

for the preparation of a drug for preventing and/or treating disorders caused by Shiga toxins and related toxins.

Shiga toxins and related toxins include the Shiga toxin (Stx) produced by *Shigella dysenteriae*, Shiga-like toxin 1 and 2 (SLT-1 and 2 or Stx-1 and 2 or Verotoxin 1 and 2) produced by Shigatoxigenic group of *Escherichia coli* (STEC), which includes serotype O157:H7 and other enterohemorrhagic *E. coli* and cholera toxin (Ctx).

Disorders caused by Shiga toxins and related toxins include abdominal pain, nausea, vomiting, diarrhea, watery diarrhea, bloody diarrhea, hemolytic uremic syndrome (HUS): microangiocytopenia anemia, thrombocytopenia and nephropathy and other extra-renal complication of HUS: seizure, intracranial infarction or hemorrhage, retinal hemorrhage and encephalopathy, acute pancreatitis and cardiomyopathy.

The present invention also relates to pharmaceutically acceptable salt of compounds of formula (I) such as hydrochloride, hydrobromide, sulphate or bisulphate, phosphate or hydrogen, acetate, oxalate, benzoate, succinate, fumarate, maleate, lactate, citrates, tartrate, gluconate, methanesulphonate, benzene-sulphonate and paratoluene-sulphonate.

By halogen atom is meant the chemical elements of group VII of the periodic table of elements; including fluorine, chlorine, bromine and iodine. The preferred halogen is bromine (Br) and fluorine (F).

The term $C_1$-$C_3$ alkyl group means a linear or branched chain of 1 to 3 carbon atoms; said chain may be for example methyl, ethyl, propyl or isopropyl.

Compounds of general formula (I) may be chosen from:

149 2-(3-bromobenzylideneamino)-N-phenylbenzamide

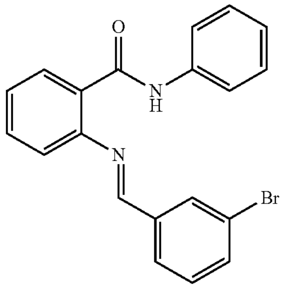 [SMILES: O=C(Nc1ccccc1)c1ccccc1/N=C/c1cccc(Br)c1]

150 2-(3-bromobenzylamino)-N-phenylbenzamide

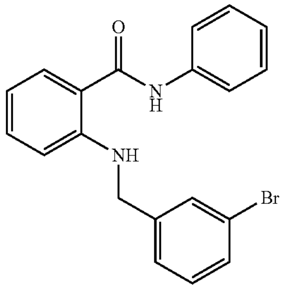 [SMILES: O=C(Nc1ccccc1)c1ccccc1NCc1cccc(Br)c1]

151 2-(3-fluorobenzylideneamino)-N-phenylbenzamide

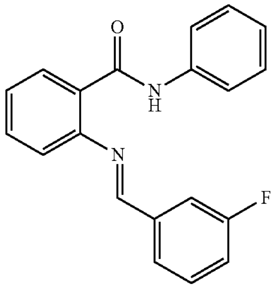 [SMILES: O=C(Nc1ccccc1)c1ccccc1/N=C/c1cccc(F)c1]

-continued
152 (E)-2-((furan-2-yl)methyleneamino)-N-phenylbenzamide
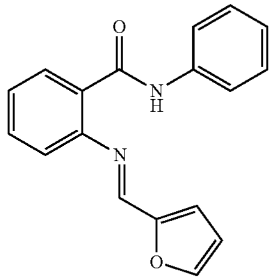 [SMILES: O=C(Nc1ccccc1)c1ccccc1/N=C/c1ccco1]
153 (E)-2-((furan-3-yl)methyleneamino)-N-phenylbenzamide
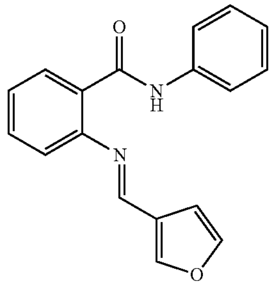 [SMILES: O=C(Nc1ccccc1)c1ccccc1/N=C/c1ccoc1]
154 (E)-2-((5-methylfuran-2-yl)methyleneamino)-N-phenylbenzamide
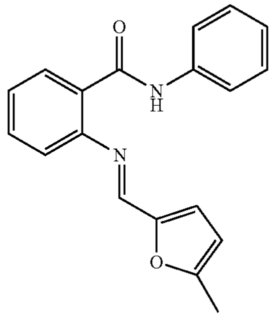 [SMILES: Cc1ccc(/C=N/c2ccccc2C(=O)Nc2ccccc2)o1]
155 (E)-2-(5-fluoro-2-nitrobenzylideneamino)-N-phenylbenzamide
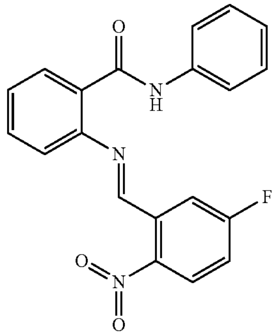 [SMILES: O=C(Nc1ccccc1)c1ccccc1/N=C/c1cc(F)ccc1[N+](=O)[O-]]
156 (E)-2-(4-fluorobenzylideneamino)-N-phenylbenzamide
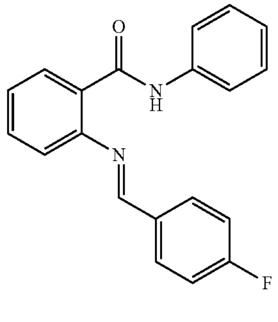 [SMILES: O=C(Nc1ccccc1)c1ccccc1/N=C/c1ccc(F)cc1]

-continued
157 (E)-2-(2-fluorobenzylideneamino)-N-phenylbenzamide
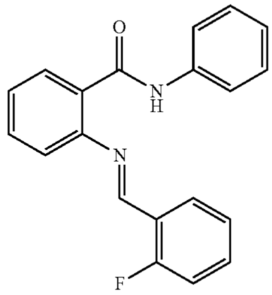 [SMILES: O=C(Nc1ccccc1)c1ccccc1/N=C/c1ccccc1F]
158 (E)-2-((1-methyl-1H-indol-2-yl)methyleneamino)-N-phenylbenzamide
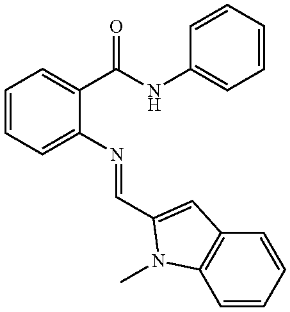 [SMILES: Cn1c(/C=N/c2ccccc2C(=O)Nc2ccccc2)cc2ccccc21]
159 (E)-2-(5-bromo-2-hydroxybenzylideneamino)-N-phenylbenzamide
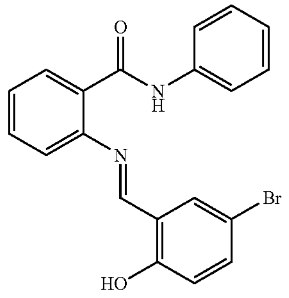 [SMILES: O=C(Nc1ccccc1)c1ccccc1/N=C/c1cc(Br)ccc1O]
160 2-(2-fluorobenzylamino)-N-phenylbenzamide
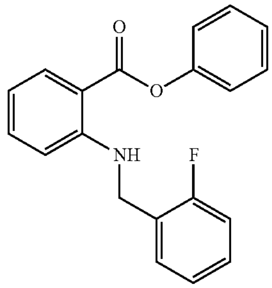 [SMILES: O=C(Oc1ccccc1)c1ccccc1NCc1ccccc1F]
161 (E)-2-(2-(5-methylthiophen-2-yl)vinyl)-N-phenylbenzamide
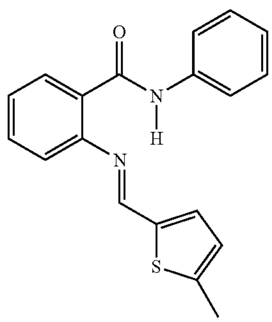 [SMILES: Cc1ccc(/C=N/c2ccccc2C(=O)Nc2ccccc2)s1]

The preparation of said imine derivatives is achieved by adding a solution of an amine in methanol to an aldehyde, said amine and aldehyde being chosen according to the imine derivative to prepare, and the mixture is stirred for 2 days. The imine derivatives are obtained after evaporation and purification.

The evaporation is performed as follows: a solution of imine in methanol is added on $BH_3CN$ resin (3 equiv.) and AcOH. After 3 days at room temperature (15-25° C.), the mixture is filtered, washed with methanol and then concentrated under vacuum. The crude compound thus obtained is purified by conventional methods.

The present invention also relates to the use of a benzodiazepine derivative of formula (II):

(II)

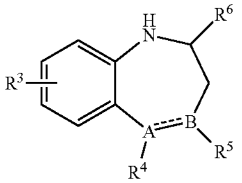

wherein

A and B are a carbon atom or a nitrogen atom with the proviso that when A=N then B═C and when A=C then B═N;

$R^3$ is chosen amongst a hydrogen atom, a halogen atom, a $C_1$-$C_6$ alkyl group, a $C_1$-$C_6$ alcoxy group, a $C_1$-$C_6$ acyloxy group, an aryloxy group, a heteroaryloxy group; these groups being optionally substituted by a $C_1$-$C_6$ alcoxy group or a heteroaryloxy group;

$R^4$ is either a link or chosen amongst a hydrogen atom, a $C_1$-$C_3$ acyloxy group, a $C_1$-$C_3$ alcoxy group or a phenyl group;

$R^5$ is either a link or chosen amongst a hydrogen atom, a $C_1$-$C_3$ alcoxy group, a $C_1$-$C_3$ acyloxy group, a $C_1$-$C_3$ alkyl group, saturated or not, optionally substituted by a phenyl group, or a phenyl group; phenyl group being optionally substituted by one or more radicals chosen amongst: —OH, a halogen atom, a $C_1$-$C_3$ alkyl group, a $C_1$-$C_3$ alcoxy group, $—NO_2$, $—CF_3$, and

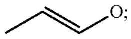;

with the proviso that $R^4$ and $R^5$ can not simultaneously be a link and when $R^4$ or $R^5$ is a link then A and B are linked by a double bound, $R^5$ may also form with the adjacent hydrogen atom a cycle of 5 or 6 atoms optionally substituted by a phenyl group; optionally interrupted by a nitrogen, oxygen or sulfur atom; preferably, it is a 5-atom cycle comprising an oxygen atom;

$R^6$ represents an oxygen atom or one or two $C_1$-$C_3$ alkyl groups;

for the preparation of a drug for preventing and/or treating disorders caused by Shiga toxins and related toxins.

The invention also relates to pharmaceutically acceptable salts of compounds of general formula (II).

The $C_1$-$C_6$ alkyl group means a linear or branched chain of 1 to 6 carbon atoms; such radical includes for example methyl, ethyl, propyl or isopropyl. The $C_1$-$C_3$ alkyl group means a linear or branched chain of 1 to 3 carbon atoms.

$C_1$-$C_6$ alcoxy group means a $—OC_mH_{2m+1}$ group, m being an integer between 1 and 6.

$C_1$-$C_3$ alcoxy group means a $—OC_{m'}H_{2m'+1}$ group, m' being an integer between 1 and 3.

$C_1$-$C_6$ acyloxy group means a $—O(CO)C_nH_{2n+1}$ or $—(CO)OC_nH_{2n+1}$ group, n being an integer between 1 and 6.

$C_1$-$C_3$ acyloxy group means a $—O(CO)C_{n'}H_{2n'+1}$ or $—(CO)OC_{n'}H_{2n'+1}$ group, n' being an integer between 1 and 3.

An aryloxy group is an aryl group linked by an oxygen atom to the rest of the compound.

A heteroaryloxy group is a heteroaryl linked by an oxygen atom to the rest of the compound.

Preferred compounds of formula (II) are such that $R_3$ is a link and/or $R_4$ is a hydrogen atom and/or $R_5$ is a phenyl group and/or when A is a carbon atom, then $R_4$ is a phenyl group and/or when B is a carbon atom then $R_5$ is a phenyl group.

Compounds of general formula (II) may be chosen from:

| | | |
|---|---|---|
| 162 | 5-phenyl-2,3-dihydro-1H-1,4-benzodiazepin-2-one | 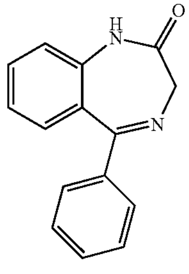 [SMILES: O=C1CN=C(c2ccccc2)c2ccccc2N1] |
| 163 | 7-bromo-5-phenyl-2,3-dihydro-1H-1,4-benzodiazepin-2-one | 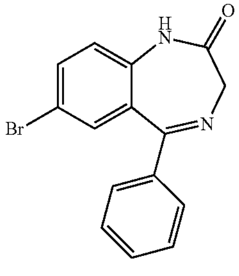 |

-continued
164 7-bromo-5-phenyl-2,3,4,5-tetrahydro-1H-1,4 -benzodiazepin-2-one
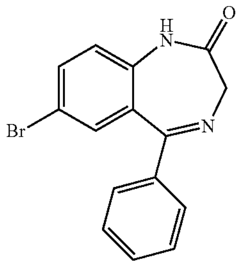
165 4-phenyl-2,3-dihydro-1H-1,5-benzodiazepin-2-one
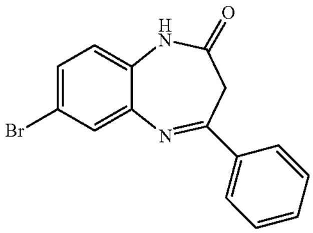 [SMILES: O=C1CC(c2ccccc2)=Nc2cc(Br)ccc2N1]
166 4-phenyl-2,3,4,5-tetrahydro-1H-1,5-benzodiazepin-2-one
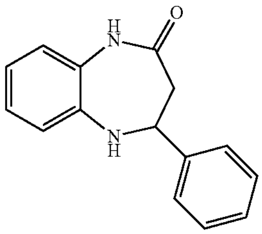
167 4,5-dihydro-7-methoxy-5-phenyl-1H-benzo[e][1,4]diazepin-2(3H)-one
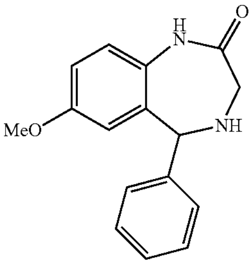 [SMILES: COc1ccc2c(c1)C(c1ccccc1)NCC(=O)N2]
168 Ethyl 4-oxo-2-phenyl-2,3,4,5-tetrahydro-1H-1,5-benzodiazepine-1-carboxylate
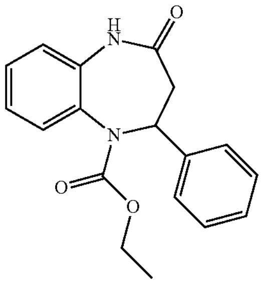 [SMILES: CCOC(=O)N1c2ccccc2NC(=O)CC1c1ccccc1]
169 5-phenyl-2,3,4,5-tetrahydro-1H-1,4-benzodiazepin-2-one
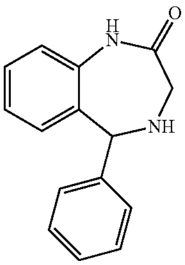 [SMILES: O=C1CNC(c2ccccc2)c2ccccc2N1]

-continued
170 7-chloro-5-phenyl-2,3-dihydro-1H-1,4-benzodiazepin-2-one
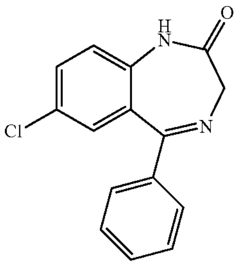 [SMILES: O=C1CN=C(c2ccccc2)c2cc(Cl)ccc2N1]
171 7-chloro-5-phenyl-2,3,4,5-tetrahydro-1H-1,4-benzodiazepin-2-one
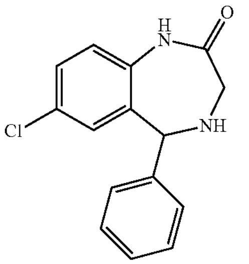 [SMILES: O=C1CNC(c2ccccc2)c2cc(Cl)ccc2N1]
172 4-(2-hydroxyphenyl)-1H-benzo[b][1,4]diazepin-2(3H)-one
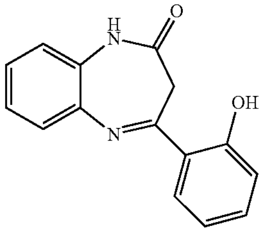 [SMILES: O=C1CC(c2ccccc2O)=Nc2ccccc2N1]
173 4-(5-bromo-2-hydroxyphenyl)-1H-benzo[b][1,4]diazepin-2(3H)-one
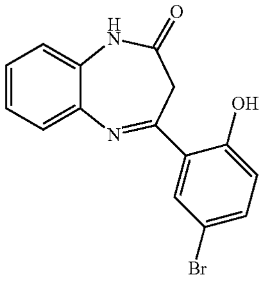 [SMILES: O=C1CC(c2cc(Br)ccc2O)=Nc2ccccc2N1]
174 4-(5-fluoro-2-hydroxyphenyl)-1H-benzo[b][1,4]diazepin-2(3H)-one
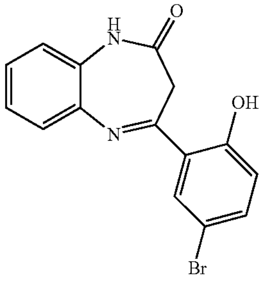 [SMILES: O=C1CC(c2cc(Br)ccc2O)=Nc2ccccc2N1]
175 8-bromo-3-phenyl-3,3a,5,10-tetrahydrobenzo[b]pyrrolo[2,3-e][1,4]diazepin-4(2H)-one
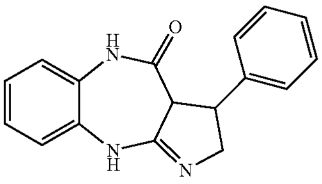 [SMILES: O=C1Nc2ccccc2NC2=NCC(c3ccccc3)C12]

-continued
176 4-m-tolyl-1H-benzo[b][1,4]diazepin-2(3H)-one
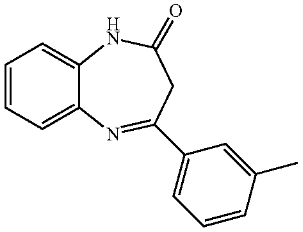 [SMILES: Cc1cccc(C2=Nc3ccccc3NC(=O)C2)c1]
177 4-(3-methoxyphenyl)-1H-benzo[b][1,4]diazepin-2(3H)-one
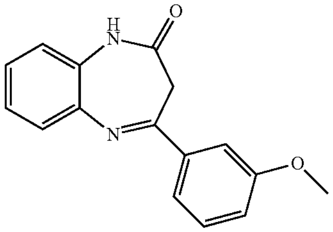 [SMILES: COc1cccc(C2=Nc3ccccc3NC(=O)C2)c1]
178 4-(3-nitrophenyl)-1H-benzo[b][1,4]diazepin-2(3H)-one
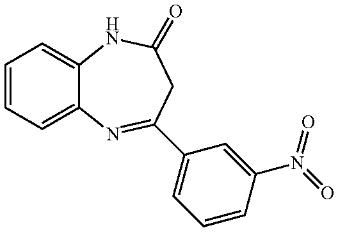 [SMILES: O=C1CC(c2cccc([N+](=O)[O-])c2)=Nc2ccccc2N1]
179 4-(3-chlorophenyl)-1H-benzo[b][1,4]diazepin-2(3H)-one
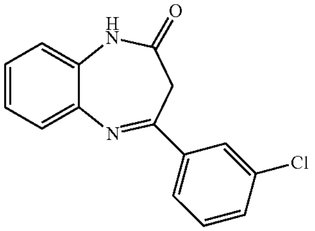 [SMILES: O=C1CC(c2cccc(Cl)c2)=Nc2ccccc2N1]
180 4-(3-bromophenyl)-1H-benzo[b][1,4]diazepin-2(3H)-one
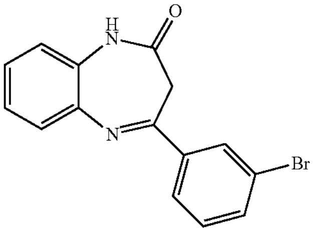 [SMILES: O=C1CC(c2cccc(Br)c2)=Nc2ccccc2N1]
181 4-(3-(trifluoromethyl)phenyl)-1H-benzo[b][1,4]diazepin-2(3H)-one
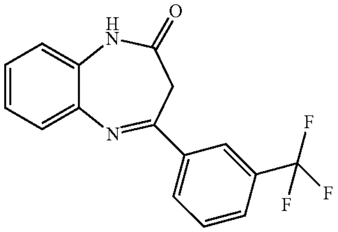 [SMILES: O=C1CC(c2cccc(C(F)(F)F)c2)=Nc2ccccc2N1]

-continued
182 7-bromo-4-m-tolyl-1H-benzo[b][1,4]diazepin-2(3H)-one
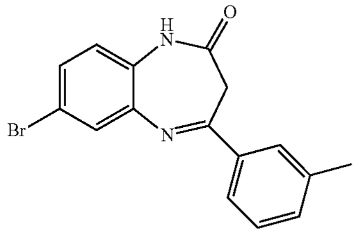 [SMILES: Cc1cccc(C2=Nc3cc(Br)ccc3NC(=O)C2)c1]
183 7-bromo-4-(3-methoxyphenyl)-1H-benzo[b][1,4]diazepin-2(3H)-one
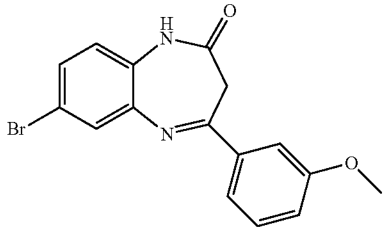 [SMILES: COc1cccc(C2=Nc3cc(Br)ccc3NC(=O)C2)c1]
184 7-bromo-4-(3-nitrophenyl)-1H-benzo[b][1,4]diazepin-2(3H)-one
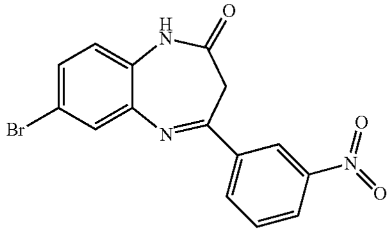 [SMILES: O=C1CC(c2cccc([N+](=O)[O-])c2)=Nc2cc(Br)ccc2N1]
185 7-bromo-4-(3-chlorophenyl)-1H-benzo[b][1,4]diazepin-2(3H)-one
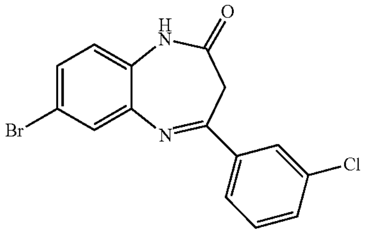 [SMILES: O=C1CC(c2cccc(Cl)c2)=Nc2cc(Br)ccc2N1]
186 7-bromo-4-(3-bromophenyl)-1H-benzo[b][1,4]diazepin-2(3H)-one
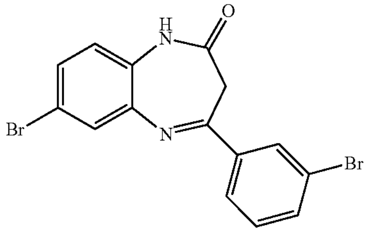
187 7-bromo-4-(3-(trifluoromethyl)phenyl)-1H-benzo[b][1,4]diazepin-2(3H)-one
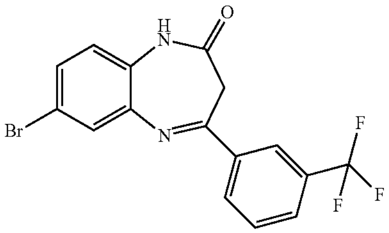 [SMILES: O=C1CC(c2cccc(C(F)(F)F)c2)=Nc2cc(Br)ccc2N1]
188 7-bromo-2,2,4-trimethyl-2,3-dihydro-1H-benzo[b][1,4]diazepine
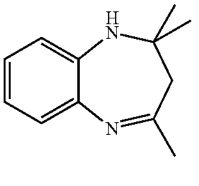

-continued 189 (E)-7-bromo-2,2-dimethyl-4-styryl-2,3-dihydro-1H-benzo[b][1,4]diazepine

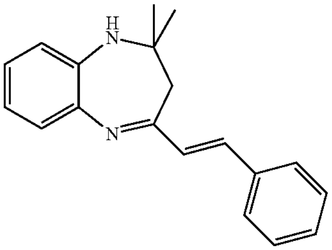 [SMILES: CC1(C)CC(/C=C/c2ccccc2)=Nc2ccccc2N1]

190 (E)-7-bromo-4-(3-bromostyryl)-2,2-dimethyl-2,3-dihydro-1H-benzo[b][1,4]diazepine

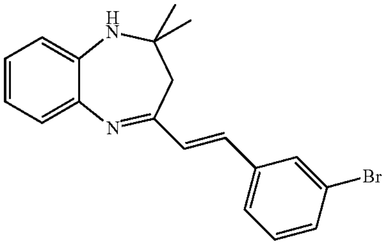 [SMILES: CC1(C)CC(/C=C/c2cccc(Br)c2)=Nc2ccccc2N1]

193 7-bromo-5-phenyl-4-propionyl-4,5-dihydro-1H-benzo[e][1,4]diazepin-2(3H)-one

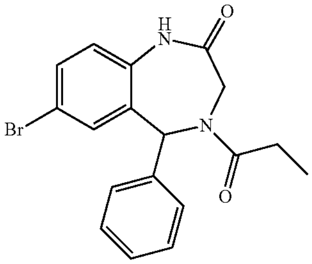 [SMILES: CCC(=O)N1CC(=O)Nc2ccc(Br)cc2C1c1ccccc1]

The synthesis of compounds of general formula (II) according to the invention is described in example 1.

In particular, derivatives benzo[e][1,4]diazepine and derivatives benzo[b][1,4]diazepine of general formula (II) are prepared as follows:

adding to a suspension of diamine, chosen according to the compound of general formula (II) to be prepared, for example, benzene-1,2-diamine or 4-bromobenzene-1,2-diamine (1 equiv.), a β-ketoester (1 equiv.) in toluene (2 ml);

stirring the mixture to reflux (120° C.) for 3 hours;

diluting the mixture in ethyl acetate, acidification (pH 5) and extraction with ethyl acetate;

filtering, evaporating and washing with diethyl ether.

Inventors have demonstrated that compounds of the invention, in particular, compounds 161 and 193 (see Example 2), are able to block specifically the retrograde route used by bacterial toxins (Shiga and Cholera toxins) and potently block Stx cytotoxicity (100-fold inhibition).

Compounds according to the present invention present thus an interest for the prevention and/or treatment of mammals, such as human, against disorders caused by Shiga toxins and related toxins by any route of administration.

The skilled person will adapt the formulation of compounds of general formula (I) and (II) according to their physicochemical properties and their route of administration.

The drug can be administered orally, parenterally, through the lung, ocularly, nasally . . . . Compounds (I) and (II) are preferably administered nasally, through the lung, orally or parenterally.

The amount of compound of formula (I) or (II) administered to the mammal depends on activity of the compound, which may be measured in ways that are described in the examples. This quantity also depends on the severity of the pathology to treat, including the amount of Shiga toxin or related toxins producing bacteria absorbed; it finally depends on the age and weight of the individual to be treated.

The use of compounds of general formula (I) or (II) is particularly advantageous for treating disorders caused by Shiga toxins and related toxins using the route of internalization to infect the cell.

In addition to the above provisions, the invention also comprises other provisions which will become clear from the description which follows, which refers to examples illustrating the biological activity of compounds of general formula (I) and (II), and also to the attached drawings in which.

EXAMPLE 1

Figure 1:
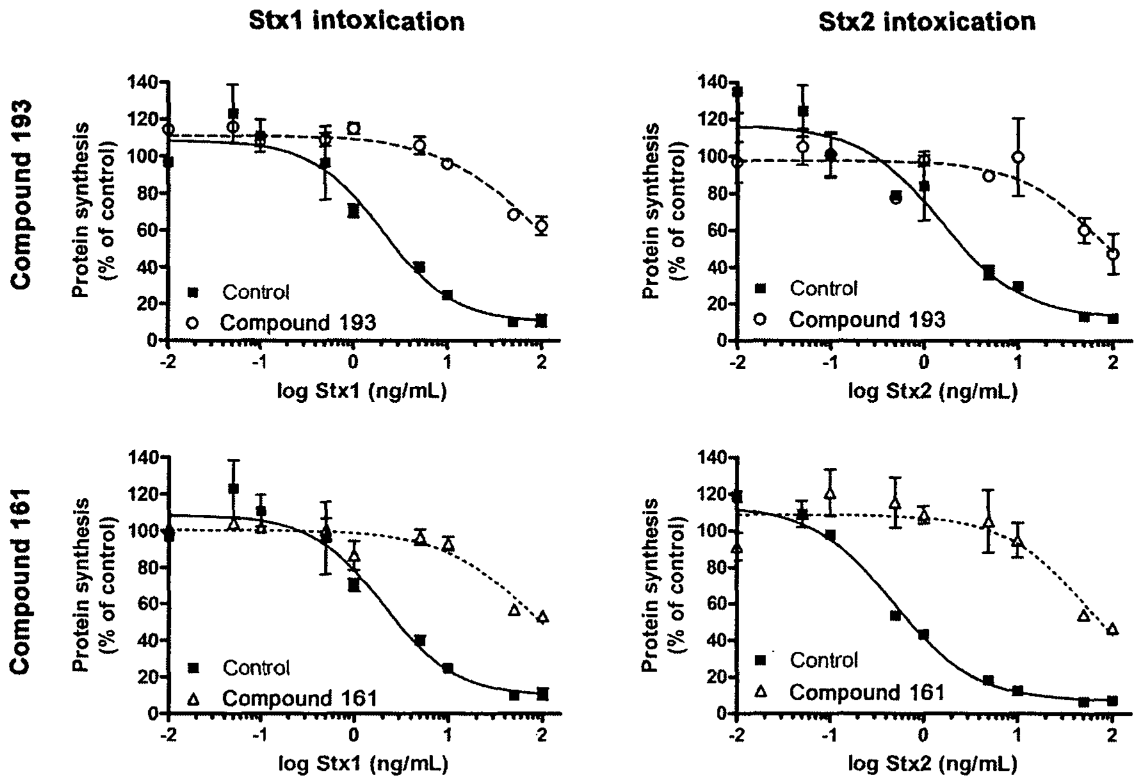
FIG. 1 is a graph representing the intoxication of HeLa cells with Stxs in the absence (control) or presence of compounds 161 and 193.

Synthesis of Compounds According to the Invention

Commercial reagents were purchased from Sigma-Aldrich and were used without prior purification. All reactions were performed under nitrogen with freshly distilled dry solvents and glassware dried in an oven.

The purification methods used for the preparation of the compounds are either filtration, Short pad (small column with silica already conditioned), column chromatography on silica gel, HPLC, crystallization or water Treatment and separation.

$^1$H NMR was performed with a Brucker Advance 400 MHz with a BBO probe. Solvents are specified for each experiment. The chemical displacements are given in parts per million (ppm), compared to the internal reference (TMS). The data are listed in the following order: δ, chemical shift, multiplicity (s: singlet, d: doublet, t: triplet, q: quadruplet, m: multiplet), integration, coupling constants (J in Hertz, Hz).

Analysis of LC/MS were performed by HPLC (High Pressure Liquid Chromatography) coupled with a mass spectrometer WATERS® AUTOPURIF. Ionization is obtained by electronical collision or by electrochemical ionization. The data are obtained as m/z.

Column: Xbridge C18 3-5 μM, 4.6 mm*100 mm

Flow rate: 1.0 mL/min

Detectors:

Photodiode array detector Waters 2996: UV (200-400 nm), PL-ELS 1000,

MS ZQ 2000.

Injection volume: 1 uL with Autosampler Waters 2767

Method: 95% solution A (99.99% water, 0.01% formic acid), 5% B (100% acetonitrile) to 0% A, B on 100% gradient of 8 minutes and 5 minutes of landing.

The column chromatographies were carried out with silica gel Merck (particle size: 230-400 mesh). All reactions were monitored by thin layer chromatography plates with preenduites silica gel 0.2 mm thick 60G-264 (Merck). The revelation was performed with a UV lamp or iodine.

Imine Derivatives

Amination

To a solution of nitroacid (8 g; 47.9 mmol; 1 equiv.) in $CH_2Cl_2$ (100 mL) were added DCC (10.9 g; 52.7 mmol; 1.1 equiv.), DMAP (1.17 g, 9.6 mmol, 0.2 equiv.) and aniline (6.1 mL; 67.1 mmol; 1.4 equiv.) at room temperature. The mixture was stirred 4 days and evaporated. The solid was taken in aceton and was filtered.

The brown filtrate was evaporated to give a brown solid which was washed with $Et_2O$ to give 2-nitro-N-phenylbenzamide as an orange solid (11.6 g; 71%).

To a solution of 2-nitro-N-phenylbenzamide (5 g; 20.7 mmol; 1 equiv.) in MeOH (65 mL) was added palladium on charcoal (550 mg) and decaborane (757 mg; 6.2 mmol; 0.3 equiv.) at room temperature. The mixture was heated at 60° C. for 6 hours, filtered over celite, washed with AcOEt and evaporated to give 2-amino-N-phenylbenzamide as brown solid (4.2 g; 96%) which was used without further purification.

To a solution of 2-amino-N-phenylbenzamide (42 mg; 0.2 mmol; 1 equiv.) in MeOH (2 mL) was added aldehyde (0.2 mmol; 1 equiv.) and the mixture was stirred 2 days at room temperature, evaporated and purified by appropriate method if necessary.

This process allows the synthesis of the following compounds:

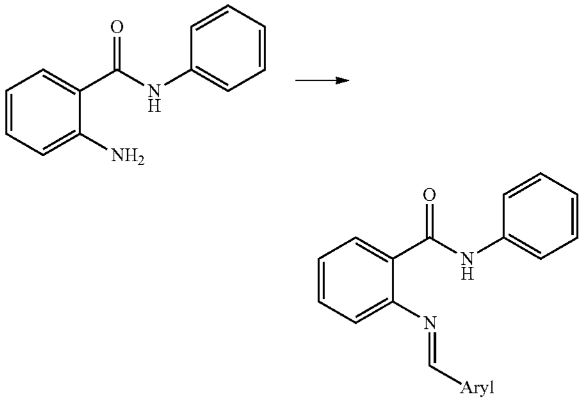

Preparation of (E)-2-((furan-2-yl)methyleneamino)-N-phenylbenzamide (compound 152)

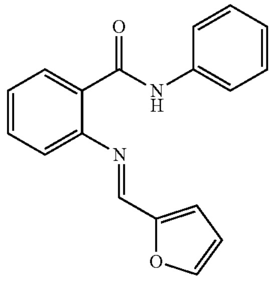 [SMILES: O=C(Nc1ccccc1)c1ccccc1/N=C/c1ccco1]

From furan-2-carbaldehyde, a yellow solid (99%) is obtained $^1$H NMR ($CDCl_3$, 400 MHz): δ 8.02 (dd, 1H, J=1.2 and 8 Hz), 7.40-7.24 (m, 7H), 6.91 (t, 1H, J=8 Hz), 6.70 (d, 1H, J=8 Hz), 6.33 (d, 1H, J=3.2 Hz), 6.25 (dd, 1H, J=2 and 3.2 Hz), 6.06 (d, 1H, J=2 Hz), 4.94 (bs, 1H).

$^{13}$C NMR ($CDCl_3$, 100 MHz): δ 162.6, 152.2, 145.1, 142.6, 140.6, 133.7, 128.9, 128.8, 126.7, 126.1, 119.7, 117.1, 115.1, 110.3, 109.0, 68.4.

ESI+MS: calcd for $C_{18}H_{14}N_2O_2$: 290.11; found: 291.1 ($MH^+$)

Preparation of (E)-2-((5-methylfuran-2-yl)methyleneamino)-N-phenylbenzamide (compound 154)

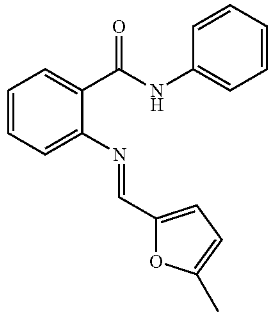 [SMILES: Cc1ccc(/C=N/c2ccccc2C(=O)Nc2ccccc2)o1]

From 5-methylfuran-2-carbaldehyde, a yellow solid (100%) is obtained. ESI+MS: calcd for $C_{19}H_{16}N_2O_2$: 304.12; found: 305.0 ($MH^+$)

Preparation of (E)-2-((furan-3-yl)methyleneamino)-N-phenylbenzamide (compound 153)

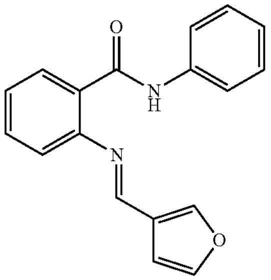 [SMILES: O=C(Nc1ccccc1)c1ccccc1/N=C/c1ccoc1]

From furan-3-carbaldehyde, a yellow solid (97%) is obtained.

$^1H$ NMR ($CDCl_3$, 400 MHz): δ 8.02 (d, 1H, J=7.6 Hz), 7.39-7.23 (m, 7H), 6.93 (t, 1H, J=7.6 Hz), 6.70 (d, 1H, J=8 Hz), 6.28 (s, 1H), 6.04 (s, 1H), 4.70 (bs, 1H).

$^{13}C$ NMR ($CDCl_3$, 100 MHz): δ 162.7, 145.5, 143.6, 140.8, 140.4, 133.8, 129.0, 128.9, 126.9, 126.7, 125.5, 119.7, 117.1, 115.2, 108.7, 67.7.

ESI+MS: calcd for $C_{18}H_{14}N_2O_2$: 290.11; found: 291.1 ($MH^+$)

Preparation of (E)-2-(2-fluorobenzylideneamino)-N-phenylbenzamide (compound 157)

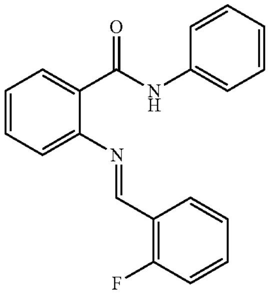 [SMILES: O=C(Nc1ccccc1)c1ccccc1/N=C/c1ccccc1F]

From 2-fluorobenzaldehyde, a yellow solid (53%) is obtained. ESI+MS: calcd for $C_{20}H_{15}FN_2O$: 318.12; found: 319.1 ($MH^+$)

Preparation of (E)-2-(3-fluorobenzylideneamino)-N-phenylbenzamide (compound 151)

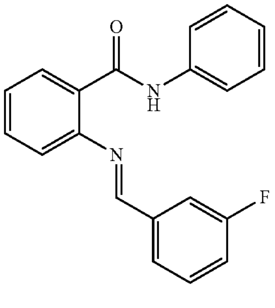 [SMILES: O=C(Nc1ccccc1)c1ccccc1/N=C/c1cccc(F)c1]

From 3-fluorobenzaldehyde, this product is obtained with a yield=100% ESI+MS: calcd for $C_{20}H_{15}FN_2O$: 318.12; found: 319.1 ($MH^+$)

Preparation of (E)-2-(3-bromobenzylideneamino)-N-phenylbenzamide (compound 149)

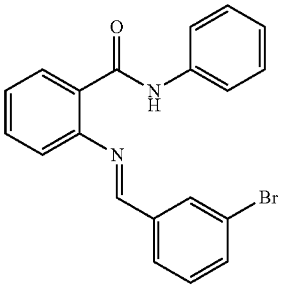 [SMILES: O=C(Nc1ccccc1)c1ccccc1/N=C/c1cccc(Br)c1]

From 3-bromobenzaldehyde, this product is obtained with a yield=100%

$^1H$ NMR (DMSO-$d^6$, 400 MHz): δ 8.40 (s, 1H), 7.70-6.60 (m, 13H, H).

Preparation of (E)-2-(4-fluorobenzylideneamino)-N-phenylbenzamide (compound 156)

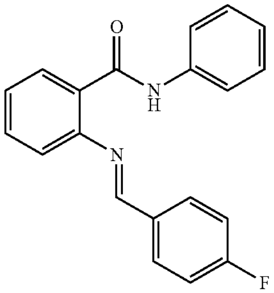 [SMILES: O=C(Nc1ccccc1)c1ccccc1/N=C/c1ccc(F)cc1]

From 4-fluorobenzaldehyde, a yellow oil (8%) is obtained.

$^1H$ NMR (DMSO $d^6$, 400 MHz): δ 9.43 (s, 1H), 7.62-6.72 (m, 13H)

ESI+MS: calcd for $C_{20}H_{15}BrN_2O$: 318.12; found: 319.2 ($MH^+$)

Preparation of (E)-2-(5-fluoro-2-nitrobenzylideneamino)-N-phenylbenzamide (compound 155)

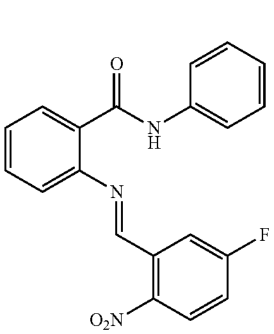 [SMILES: O=C(Nc1ccccc1)c1ccccc1/N=C/c1cc(F)ccc1[N+](=O)[O-]]

From 5-fluoro-2-nitrobenzaldehyde, a yellow oil (2.9%) is obtained.

ESI+MS: calcd for $C_{20}H_{14}FN_3O_3$: 363.34; found: 364.1 ($MH^+$)

Preparation of (E)-2-(5-bromo-2-hydroxybenzylideneamino)-N-phenylbenzamide (compound 159)

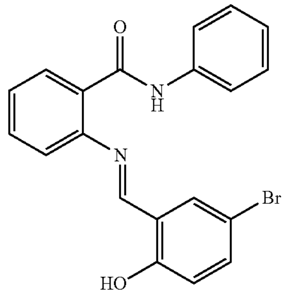 [SMILES: O=C(Nc1ccccc1)c1ccccc1/N=C/c1cc(Br)ccc1O]

From 5-bromo-2-hydroxybenzaldehyde, a yellow oil (92%) is obtained.

ESI+MS: calcd for $C_{20}H_{15}BrN_2O_2$: 394.03; found: 395.0 ($MH^+$)

Preparation of (E)-2-((1-methyl-1H-indol-2-yl)methyleneamino)-N-phenylbenzamide (compound 158)

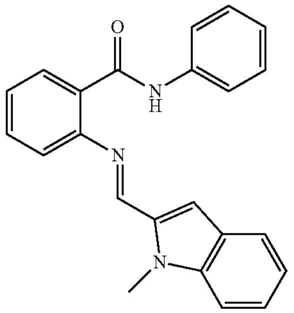 [SMILES: Cn1c(/C=N/c2ccccc2C(=O)Nc2ccccc2)cc2ccccc21]

From 1-methyl-1H-indole-2-carbaldehyde, a yellow oil (12%) is obtained.

ESI+MS: calcd for $C_{23}H_{19}N_3O$: 353.15; found: 354.2 ($MH^+$)

Reductive Amination

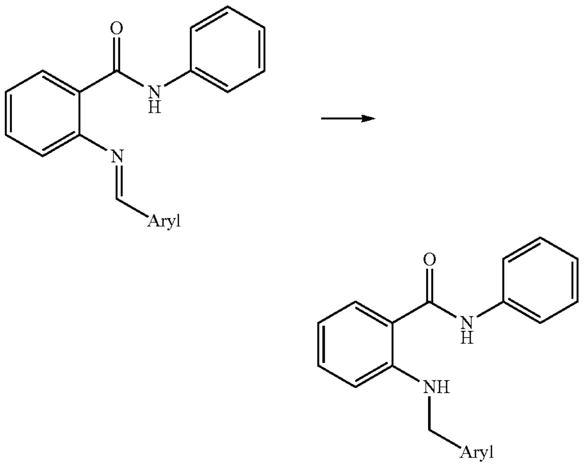

Preparation of 2-(3-bromobenzylamino)-N-phenyl benzamide (compound 150)

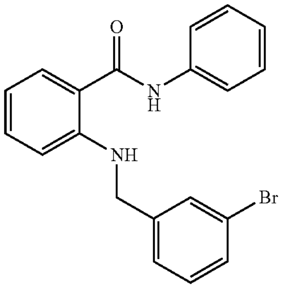 [SMILES: O=C(Nc1ccccc1)c1ccccc1NCc1cccc(Br)c1]

From (E)-2-(3-bromobenzylideneamino)-N-phenylbenzamide Yield=100%

Preparation of 2-(2-fluorobenzylamino)-N-phenylbenzamide (compound 160)

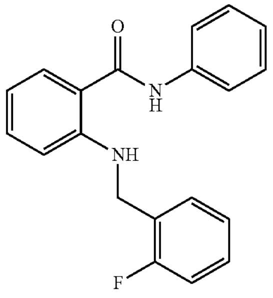 [SMILES: O=C(Nc1ccccc1)c1ccccc1NCc1ccccc1F]

From (E)-2-(2-fluorobenzylideneamino)-N-phenylbenzamide, colourless oil (1%) is obtained.

ESI+MS: calcd for $C_{20}H_{17}FN_2O$: 320.13; found: 321.0 ($MH^+$)

Benzodiazepines

Synthesis of benzo[e][1,4]diazepin

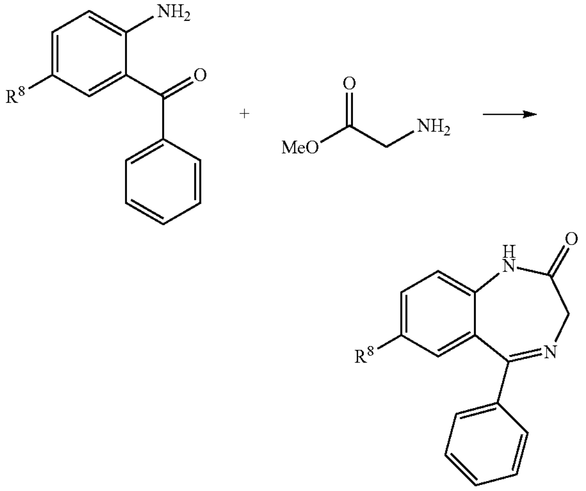

Preparation of (Z)-5-phenyl-1H-benzo[e][1,4]diazepin-2(3H)-one (compound 162)

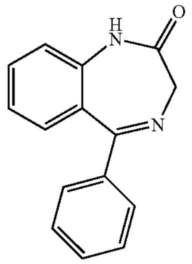 [SMILES: O=C1CN=C(c2ccccc2)c2ccccc2N1]

From (2-aminophenyl)(phenyl)methanone, the compound is obtained with a yield=53%.

$^1$H NMR ($CDCl_3$, 400 MHz): δ 48.45 (s, 1H), 7.64-7.26 (m, 9H), 4.34 (s, 2H).

ESI+MS: calcd for $C_{15}H_{12}N_2O$: 236.09; found: 237 ($MH^+$)

Preparation of (Z)-7-chloro-5-phenyl-1H-benzo[e][1,4]diazepin-2(3H)-one (compound 170)

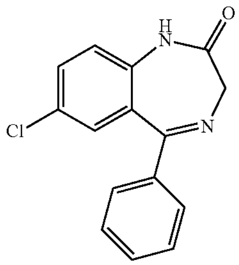 [SMILES: O=C1CN=C(c2ccccc2)c2cc(Cl)ccc2N1]

From (2-amino-5-chlorophenyl)(phenyl)methanone, the compound is obtained with a yield=17%.

$^1$H NMR ($CDCl_3$, 400 MHz,): δ 9.42 (s, 1H), 7.78-7.16 (m, 8H), 4.33 (s, 2H).

ESI+MS: calcd for $C_{15}H_{11}ClN_2O$: 270.06; found: 271 ($MH^+$)

Preparation of (Z)-7-bromo-5-phenyl-1H-benzo[e][1,4]diazepin-2(3H)-one (compound 163)

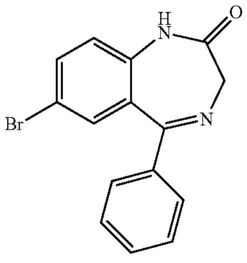

From (2-amino-5-bromophenyl)(phenyl)methanone, the compound is obtained with a yield=26%

$^1$H NMR ($CDCl_3$, 400 MHz): δ 9.26 (s, 1H), 7.90-7.32 (m, 8H), 4.37 (s, 2H).

ESI+MS: calcd for $C_{15}H_{11}BrN_2O$: 314.01; found: 315 ($MH^+$)

Synthesis of benzo[b][1,4]diazepin

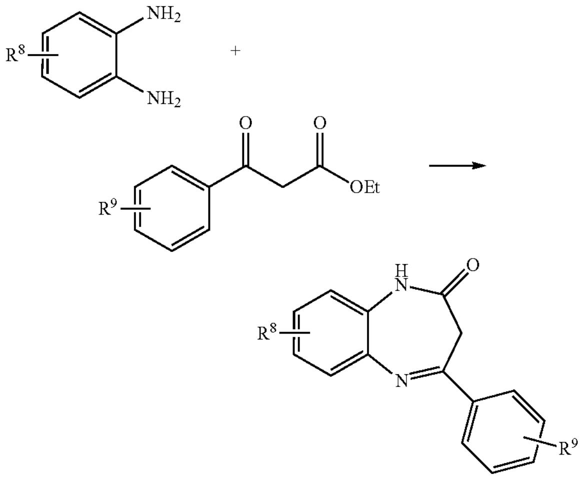

To a stirred suspension of diamine (0.5 mmol; 54 mg; 1 equiv.) in toluene (2 mL) was added β-ketoester (0.5 mmol; 1 equiv.). The mixture was stirred at reflux (120° C.) during 3 hours. The mixture was diluted with EtOAc, acidified (pH 5), extracted with EtOAc, filtered, evaporated and washed with $Et_2O$ to give the expected compound.

From benzene-1,2-diamine

Preparation of (E)-4-phenyl-1H-benzo[b][1,4]diazepin-2(3H)-one (compound 165)

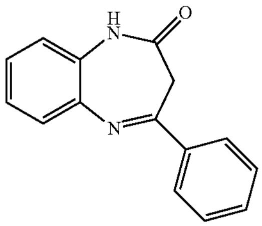 [SMILES: O=C1CC(c2ccccc2)=Nc2ccccc2N1]

From ethyl 3-oxo-3-phenylpropanoate, a colorless oil (69%) is obtained $^1$H NMR ($CDCl_3$, 400 MHz): δ 12.88 (s, 1H), 8.17-6.64 (m, 9H), 5.50 (s, 2H).

ESI+MS: calcd for $C_{15}H_{12}N_2O$: 236.09; found: 237 ($MH^+$)

Preparation of (E)-4-m-tolyl-1H-benzo[b][1,4]diazepin-2(3H)-one (compound 176)

From ethyl 3-oxo-3-m-tolylpropanoate, a brown solid (31%) is obtained $^1$H NMR ($CDCl_3$, 400 MHz): δ 7.94 (s, 1H), 7.91 (d, 1H, J=8 Hz), 7.69 (bs, 1H), 7.54 (d, 1H, J=8.8 Hz), 7.38 (t, 1H, J=7.6 Hz), 7.31 (m, 2H), 7.05 (dd, 1H, J=1.6 and 7.6 Hz), 3.59 (s, 2H), 2.45 (s, 3H).

ESI+MS: calcd for $C_{16}H_{14}N_2O$: 250.11; found: 250.1 ($MH^+$)

Preparation of (E)-4-(3-methoxyphenyl)-1H-benzo[b][1,4]diazepin-2(3H)-one (compound 177)

From ethyl 3-(3-methoxyphenyl)-3-oxopropanoate, brown solid (20%) is obtained.

$^1H$ NMR ($CDCl_3$, 400 MHz): δ 7.68 (m, 3H), 7.55 (dd, 1H, J=2 and 8 Hz), 7.40 (t, 1H, J=8.4 Hz), 7.28 (m, 1H), 7.06 (dt, 2H, J=2.8 and 8 Hz), 3.91 (s, 3H), 3.58 (s, 2H).

$^{13}C$ NMR ($CDCl_3$, 100 MHz): δ 167.3, 159.9, 158.8, 139.8, 138.9, 129.7, 128.9, 128.3, 126.5, 125.2, 121.6, 120.4, 117.7, 112.2, 55.5, 39.9.

ESI+MS: calcd for $C_{16}H_{14}N_2O_2$: 266.11; found: 267.0 ($MH^+$)

Preparation of (E)-4-(3-nitrophenyl)-1H-benzo[b][1,4]diazepin-2(3H)-one (compound 178)

From ethyl 3-(3-nitrophenyl)-3-oxopropanoate, a brown solid (23%) is obtained.

$^1H$ NMR ($CDCl_3$, 400 MHz): δ 9.00 (t, 1H, J=2 Hz), 8.40 (d, 1H, J=8 Hz), 8.35 (dd, 1H, J=1.6 and 8 Hz), 7.73 (bs, 1H), 7.68 (t, 1H, J=8.4 Hz), 7.55 (m, 1H), 7.32 (m, 2H), 7.09 (m, 1H), 3.62 (s, 2H).

ESI+MS: calcd for $C_{15}H_{11}N_3O_3$: 281.08; found: 282.0 ($MH^+$)

Preparation of (E)-4-(3-chlorophenyl)-1H-benzo[b][1,4]diazepin-2(3H)-one (compound 179)

From ethyl 3-(3-chlorophenyl)-3-oxopropanoate, a brown solid (15%) is obtained.

$^1H$ NMR ($CDCl_3$, 400 MHz): δ 8.14 (t, 1H, J=1.6 Hz), 7.96 (d, 1H, J=7.6 Hz), 7.76 (bs, 1H), 7.53-7.41 (m, 3H), 7.29 (m, 2H), 7.07 (dd, 1H, J=1.2 and 6.8 Hz), 3.56 (s, 2H).

$^{13}C$ NMR ($CDCl_3$, 100 MHz): δ 167.1, 157.3, 139.7, 139.3, 135.0, 131.0, 129.9, 128.9, 128.4, 127.8, 126.9, 125.8, 125.3, 121.7, 39.7.

Preparation of (E)-4-(3-bromophenyl)-1H-benzo[b][1,4]diazepin-2(3H)-one (compound 180)

From ethyl 3-(3-bromophenyl)-3-oxopropanoate, a brown solid (7%) is obtained.

$^1H$ NMR ($CDCl_3$, 400 MHz): δ 8.30 (t, 1H, J=1.6 Hz), 8.00 (d, 1H, J=8 Hz), 7.77 (bs, 1H), 7.63 (dd, 1H, J=0.8 and 8 Hz), 7.52 (dd, 1H, J=2 and 7.6 Hz), 7.36 (t, 1H, J=8 Hz), 7.27 (m, 1H), 7.07 (dd, 1H, J=1.6 and 7.2 Hz), 3.55 (s, 2H).

$^{13}C$ NMR ($CDCl_3$, 100 MHz): δ 166.9, 157.3, 139.7, 139.3, 133.9, 130.7, 130.2, 128.8, 128.4, 126.9, 126.3, 125.3, 123.1, 121.7, 39.7.

Preparation of (E)-4-(3-(trifluoromethyl)phenyl)-1H-benzo[b][1,4]diazepin-2(3H)-one (compound 181)

From ethyl 3-(3-(trifluoromethyl)phenyl)-3-oxopropanoate, a brown solid (34%) is obtained.

$^1H$ NMR ($CDCl_3$, 400 MHz): δ 8.42 (s, 1H), 8.26 (d, 1H, J=7.6 Hz), 7.78 (bs, 1H), 7.76 (d, 1H, J=8.4 Hz), 7.63 (t, 1H, J=7.6 Hz), 7.54 (dd, 1H, J=2.4 and 8 Hz), 7.33-7.29 (m, 2H), 7.08 (dd, 1H, J=2.4 and 7.2 Hz), 3.60 (s, 2H).

From 4-bromobenzene-1,2-diamine

To a stirred suspension of diamine (0.5 mmol; 94 mg; 1 equiv.) in toluene (2 mL) was added β-ketoester (0.5 mmol; 1 equiv.). The mixture was stirred at reflux (120° C.) during 3 hours. The mixture was diluted with EtOAc, acidified (pH 5), extracted with EtOAc, filtered, evaporated and washed with $Et_2O$ to give the expected compound.

Preparation of (E)-7-bromo-4-m-tolyl-1H-benzo[b][1,4]diazepin-2(3H)-one (compound 182)

From ethyl 3-oxo-3-m-tolylpropanoate, a brown solid (28%) is obtained.

$^1H$ NMR ($CDCl_3$, 400 MHz): δ 7.89 (m, 3H), 7.40-7.32 (m, 4H), 3.58 (s, 2H), 2.44 (s, 3H).

ESI+MS: calcd for $C_{16}H_{13}BrN_2O$: 328.02; found: 328.9 ($MH^+$)

Preparation of (E)-7-bromo-4-(3-methoxyphenyl)-1H-benzo[b][1,4]diazepin-2(3H)-one (compound 183)

From ethyl 3-(3-methoxyphenyl)-3-oxopropanoate, a brown solid (10%) is obtained.

ESI+MS: calcd for $C_{16}H_{13}BrN_2O_2$: 344.02; found: 344.9 ($MH^+$)

Preparation of (E)-7-bromo-4-(3-nitrophenyl)-1H-benzo[b][1,4]diazepin-2(3H)-one (compound 184)

From 3-(3-nitrophenyl)-3-oxopropanoate, a brown solid (6.5%) is obtained.

ESI+MS: calcd for $C_{15}H_{10}BrN_3O_3$: 358.99; found: 359.8 ($MH^+$)

Preparation of (E)-7-bromo-4-(3-chlorophenyl)-1H-benzo[b][1,4]diazepin-2(3H)-one (compound 185)

From ethyl 3-(3-chlorophenyl)-3-oxopropanoate, a brown solid (23%) is obtained.

ESI+MS: calcd for $C_{15}H_{10}BrClN_2O$: 347.97; found: 348.8 ($MH^+$)

Preparation of (E)-7-bromo-4-(3-bromophenyl)-1H-benzo[b][1,4]diazepin-2(3H)-one (compound 186)

From ethyl 3-(3-bromophenyl)-3-oxopropanoate, a brown solid (10%) is obtained.

ESI+MS: calcd for $C_{15}H_{10}Br_2N_2O$: 391.92; found: 392.8 ($MH^+$)

Preparation of (E)-7-bromo-4-(3-(trifluoromethyl)phenyl)-1H-benzo[b][1,4]diazepin-2(3H)-one (compound 187)

From ethyl 3-(3-(trifluoromethyl)phenyl)-3-oxopropanoate, a brown solid (29%) is obtained.

ESI+MS: calcd for $C_{16}H_{10}BrF_3N_2O$: 381.99; found: 382.8 ($MH^+$)

Function Imine Reduction

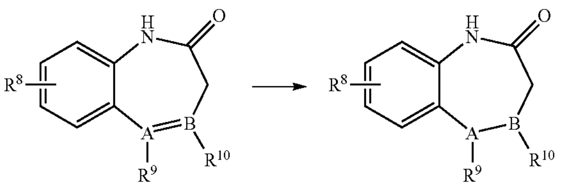

From benzo[e][1,4]diazepin:

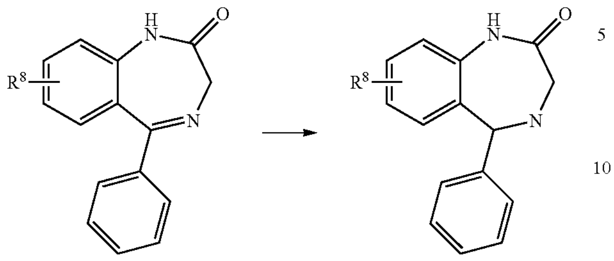

To a stirred solution of benzo[e][1,4]diazepin (1 eqv.) in MeOH was added $BH_3CN$-resin (3 eqv.) and AcOH. The mixture was stirred 3 days at room temperature, filtered, washed with methanol, evaporated and purified by appropriate method if necessary.

Preparation of 4,5-dihydro-5-phenyl-1H-benzo[e][1,4]diazepin-2(3H)-one (compound 169)

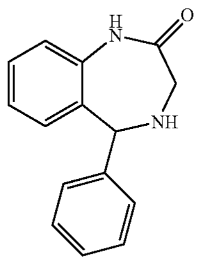 [SMILES: O=C1CNC(c2ccccc2)c2ccccc2N1]

From (Z)-5-phenyl-1H-benzo[e][1,4]diazepin-2(3H)-one (compound 162), this compound is obtained with a yield=60%

$^1$H NMR ($CDCl_3$, 400 MHz): δ 9.12 (s, 1H), 7.35-6.67 (m, 9H,), 5.21 (s, 1H), 3.35-3.25 (q, 2H, J=10-14.8 Hz), 3.21 (s, 1H).

ESI+MS: calcd for $C_{15}H_{14}N_2O$: 238.11; found: 239 ($MH^+$)

Preparation of 7-chloro-4,5-dihydro-5-phenyl-1H-benzo[e][1,4]diazepin-2(3H)-one compound 171))

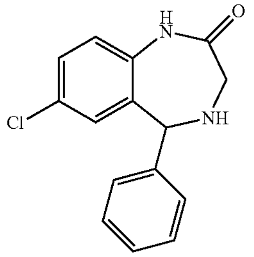

From (Z)-7-chloro-5-phenyl-1H-benzo[e][1,4]diazepin-2(3H)-one (compound 170), this compound is obtained with a yield=55%

$^1$H NMR ($CDCl_3$, 400 MHz): δ 9.15 (s, 1H), 7.40-6.86 (m, 8H), 5.20 (s, 1H), 3.45-3.36 (q, 2H, J=10-13.6 Hz), 3.10 (s, 1H).

ESI+MS: calcd for $C_{15}H_{13}ClN_2O$: 272.07; found: 273 ($MH^+$)

Preparation of 7-bromo-4,5-dihydro-5-phenyl-1H-benzo[e][1,4]diazepin-2(3H)-one (compound 164)

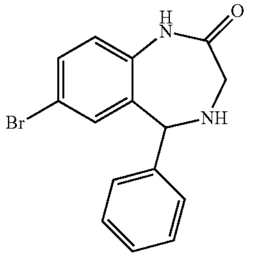 [SMILES: O=C1CNC(c2ccccc2)c2cc(Cl)ccc2N1]

From (Z)-7-bromo-5-phenyl-1H-benzo[e][1,4]diazepin-2(3H)-one (compound 163), this compound is obtained with a yield=52%

$^1$H NMR ($CDCl_3$, 400 MHz,): δ 8.48 (s, 1H), 7.52-6.86 (m, 8H), 5.18 (s, 1H), 3.45-3.35 (q, 2H, J=10-14.8 Hz), 2.86 (s, 1H).

ESI+MS: calcd for $C_{15}H_{13}BrN_2O$: 316.02; found: 317 ($MH^+$)

From benzo[b][1,4]diazepin

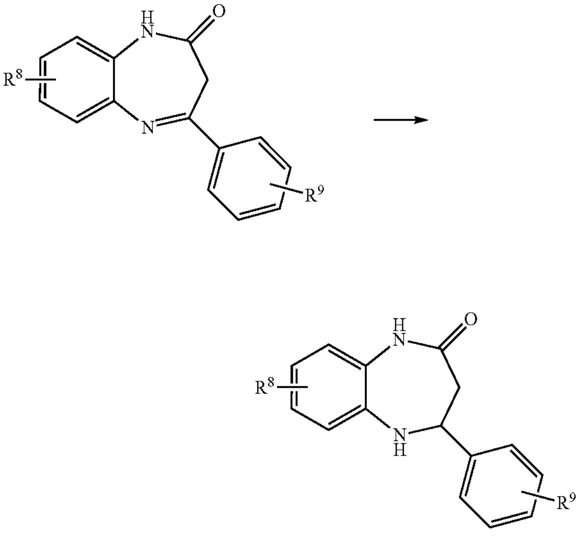

To a stirred solution of benzo[b][1,4]diazepin (1 eqv.) in MeOH was added $BH_3CN$-resin (3 eqv.) and AcOH. The mixture was stirred 3 days at room temperature, filtered, washed with methanol, evaporated and purified by appropriate method if necessary.

Preparation of 4,5-dihydro-4-phenyl-1H-benzo[b][1,4]diazepin-2(3H)-one compound 166)

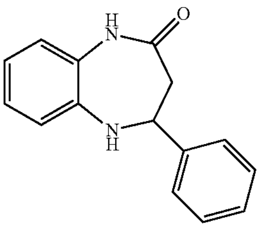 [SMILES: O=C1CC(c2ccccc2)Nc2ccccc2N1]

From (E)-4-phenyl-1H-benzo[b][1,4]diazepin-2(3H)-one (compound 165), this product is obtained with a yield=77%

$^1$H NMR ($CDCl_3$, 400 MHz,): δ 9.15 (s, 1H), 7.40-6.72 (m, 9H), 5.76 (s, 1H), 4.91-4.89 (m, 1H), 2.54-2.52 (d, 2H, J=6 Hz).

ESI+MS: calcd for $C_{15}H_{14}N_2O$: 238.11; found: 239 ($MH^+$)

N-Substitution

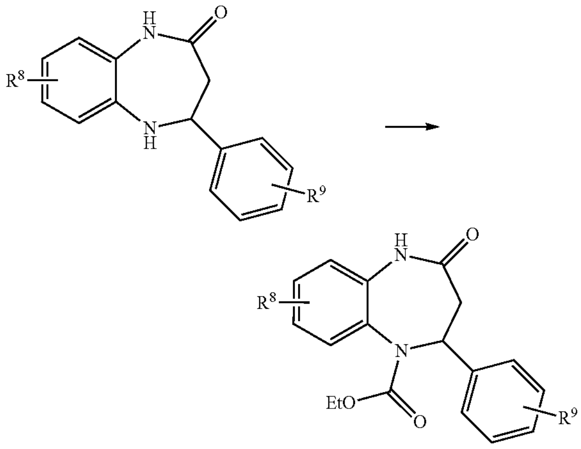

Preparation of ethyl 2,3,4,5-tetrahydro-4-oxo-2-phenylbenzo[b][1,4]diazepine-1-carboxylate (compound 168)

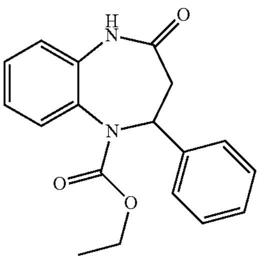 [SMILES: CCOC(=O)N1c2ccccc2NC(=O)CC1c1ccccc1]

From 4,5-dihydro-4-phenyl-1H-benzo[b][1,4]diazepin-2(3H)-one (compound 165), this product is obtained with a yield=21%

$^1$H NMR ($CDCl_3$, 400 MHz): δ 9.10 (s, 1H), 7.62-6.72 (m, 9H) 5.10 (s, 1H), 4.24 (m, 2H), 2.62-2.61 (d, 2H, J=6 Hz), 1.46 (t, 3H, J=8 Hz).

ESI+MS: calcd for $C_{18}H_{18}N_2O_3$: 310.13; found: 311 ($MH^+$)

EXAMPLE 2

Biological Activity of Compounds According to the Invention

Materials

STxB-Sulf$_2$, STxB-KDEL-Cy3, Cy3-STxB, Cy5-STxB, anti-TfR, mAb H68.4 and anti-STxB mAb 13C4 were prepared as previously described in Johannes and Goud, 1998 Trends Cell Biol 8(4): 158-62; Mallard et al. 1998 J Cell Biol 16; 143(4):973-90).

The following products were kindly provided by the indicated colleagues: plasmid GFP-Rab11 (Kazuhisa Nakayama, Kyoto University, Japan), CTR433 (Michel Bornens, Institut Curie, France), anti-Vps26 antibody (Juan Bonifacino, Bethesda, Md., USA), anti-VSVG antibody (Franck Perez, Institut Curie, France), Stx1 (Lynne Roberts, University of Warwick, UK), ricin (Bruno Beaumelle, UMR 5539 CNRS, Montpellier, France).

The following products were purchased from the indicated commercial sources: $^{125}$I-EGF, $^{35}$S-sulfate, $^{35}$S-methionine (Perkin Elmer); Alexa488-conjugated CTxB (Molecular Probes); PPMP (Calbiochem), DMSO, BFA, Stx2, 2-mercaptoethanesulfonic acid sodium salt, iodoacetamide, human diferric Tf (Sigma); horseradish peroxidase-conjugated streptavidin (Roche); NHS-SS-Biotin (Pierce). The following commercial antibodies were utilized in this study: anti-giantin (Abcam), anti-TfR (BD Biosciences), anti-EEA1 (Santa Cruz), anti-Lamp1 (BD Biosciences), anti-GFP (Roche), anti-TGN46 (AbD Serotech), anti-golgin-97 (Invitrogen), anti-GM130 (Santa Cruz), anti-mouse-Alexa488, anti-goat-Alexa488, anti-rabbit-Alexa488 (Molecular Probes), and anti-sheep-Cy3 (Jackson ImmunoResearch).

Methods

1. HELA-Cells are Protected Against STX-Intoxication

HeLa-cells were treated with 20 μM of compounds 161 or 193 before challenging them for 45 minutes at 37° C. with increasing doses of Stx1 and Stx2. Protein biosynthesis was determined 1 hour later by measuring the incorporation of radiolabeled methionine into acid-precipitable material.

Cells were washed three times with PBS and incubated in PBS containing 20 μCi/ml $^{35}$S-methionine for 60 min. Labelled proteins were precipitated with 5% (w/v) trichioroacetic acid, the wells were washed three times with PBS and the amount of radiolabel incorporated was determined after the addition of 200 μl of scintillation fluid, by scintillation counting in a Micro-Beta 1450 Trilux counter.

Compound-treated cells are dramatically protected against the intoxication by Stxs. In inhibitor-treated HeLa-cells, 50-100x higher doses of Stxs are needed to obtain a similar level of protein biosynthesis inhibition as in control cells (FIG. 1).

2. Quantification of the Retrograde Transport Inhibition of STX to the Trans-Golgi-Network (TGN) I The retrograde transport of StxB to the TGN was quantified by sulfation assay (extensively described by Amessou et al. ((2006) Curr Protoc Cell Biol Chapter 15, Unit 15 10) as early as 20 min and up to 4 h after internalization. For this assay, a StxB variant called StxB-Sulf$_2$, which bears a tandem of protein sulfation recognition sites, is internalized in the presence of $^{35}SO_4^{2-}$. Upon arrival in the TGN, the TGN-localized sulfotransferase catalyzes the transfer of radioactive sulphate onto StxB-Sulf$_2$. After cell lysis, immunoprecipitation, and gel electrophoresis, [$^{35}$S]-sulfated StxB-Sulf$_2$ can be detected and quantified by autoradiography.

Figure 2:
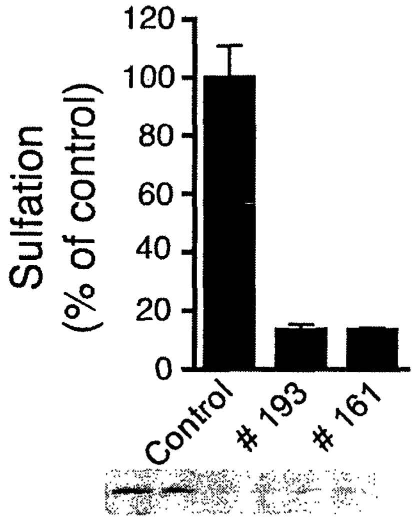
FIG. 2 shows the results of sulfation assay as described in Example 2, part 2.

On compounds 161 or 193-treated cells, the retrograde transport of STxB is dramatically reduced (90%) (FIG. 2). Even 4 h after internalization, compounds reduce transport of StxB to the TGN by 50%.

3. Transport of STX and CTX is Inhibited at the Interface Between Early Endosomes and Golgi Apparatus Immunofluorescence was used to determine at which step the retrograde transport of Stx and Ctx is inhibited. Compound-treated cells were incubated with Cy3-STxB (0.5 μg/mL) or Alexa488-CTxB (4 μg/mL) for 30 min on ice, followed by 45 min at 37° C. in the continued presence of compounds (20 μM). Cells were fixed with paraformaldehyde, and stained with compartment-specific antibodies such as EEA1, TfR, Vps26 (early endosomes), Rab11 (recycling endosomes), Lamp1 (late endosomes) and giantin (Golgi). Cells were imaged using a Leica TCS SP2 confocal microscope with HCX PL APO-objectives (100×/1.40-0.7 and 63×/1.32-0.60, Leica Microsystems, Mannheim, Germany).

Figure 3:
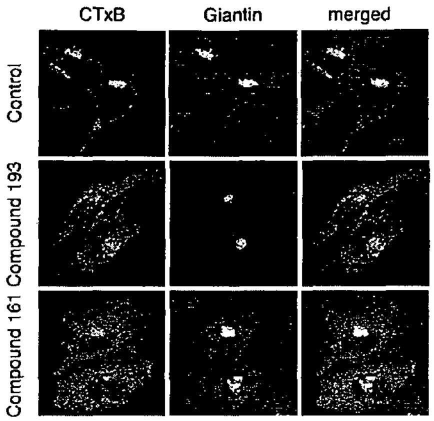
FIG. 3 shows pictures of cellular localisation of CtxB in comparison with the Golgi apparatus after inhibition with compounds according to the present invention.
Figure 4:
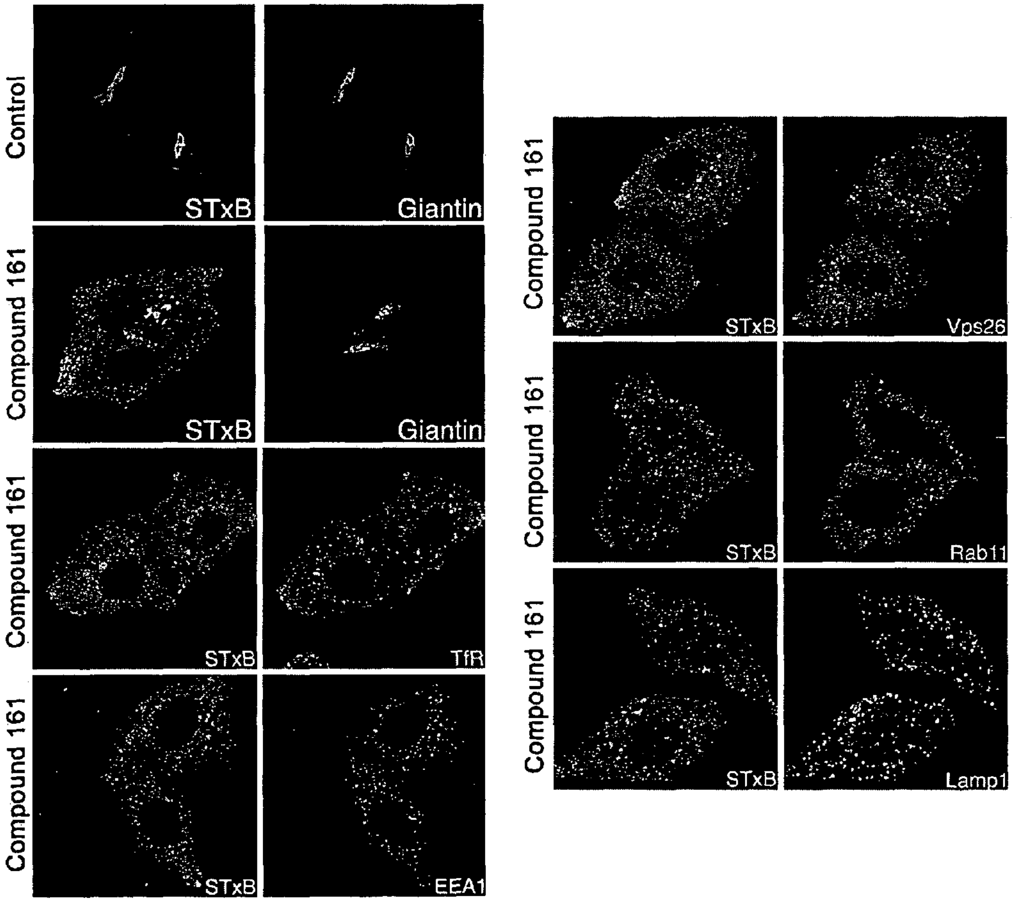
FIG. 4 shows pictures of cellular localization of STxB after incubation with compound 161.

Upon compounds-treatment, STxB accumulates in early endosomes, and the retrograde transport of CTxB and STxB to the TGN is markedly reduced (FIGS. 3 and 4).

4. Cytotoxicity of Compounds 161 and 193

For our studies on HeLa-cells, both compounds 161 and 193 were used at a final concentration of 20 μM (0.1% DMSO). Under this condition, the effect on protein biosynthesis after 2.5 h of treatment was only minor (FIG. 1, control versus compound-treated cells at infra-toxic toxin concentrations). The cell number was determined over 3 days of treatment and compound-treatment had no influence on cell growth.

5. Effects of Compounds 161 and 193 on Cellular Morphology

Cells were incubated with 20 μM of compound for 2 h, fixed with PFA and permeabilized with saponin. Antibodies directed against various cellular compartments were used for immunofluorescence to visualize the effect of compounds on early endosomes (EEA1, TfR), late endosomes/lysosomes (Lamp1), Golgi apparatus (giantin, golgin-97, CTR433, GM130) and the ER. For the ER-staining, the following protocol was applied: internalization of STxB-KDEL-Cy3 in the absence of inhibitors for 4 h. During this time, STxB-KDEL-Cy3 accumulates in the ER. Then, cells were treated for 2 h with DMSO, Compound 161 or Compound 193.

Figure 5:
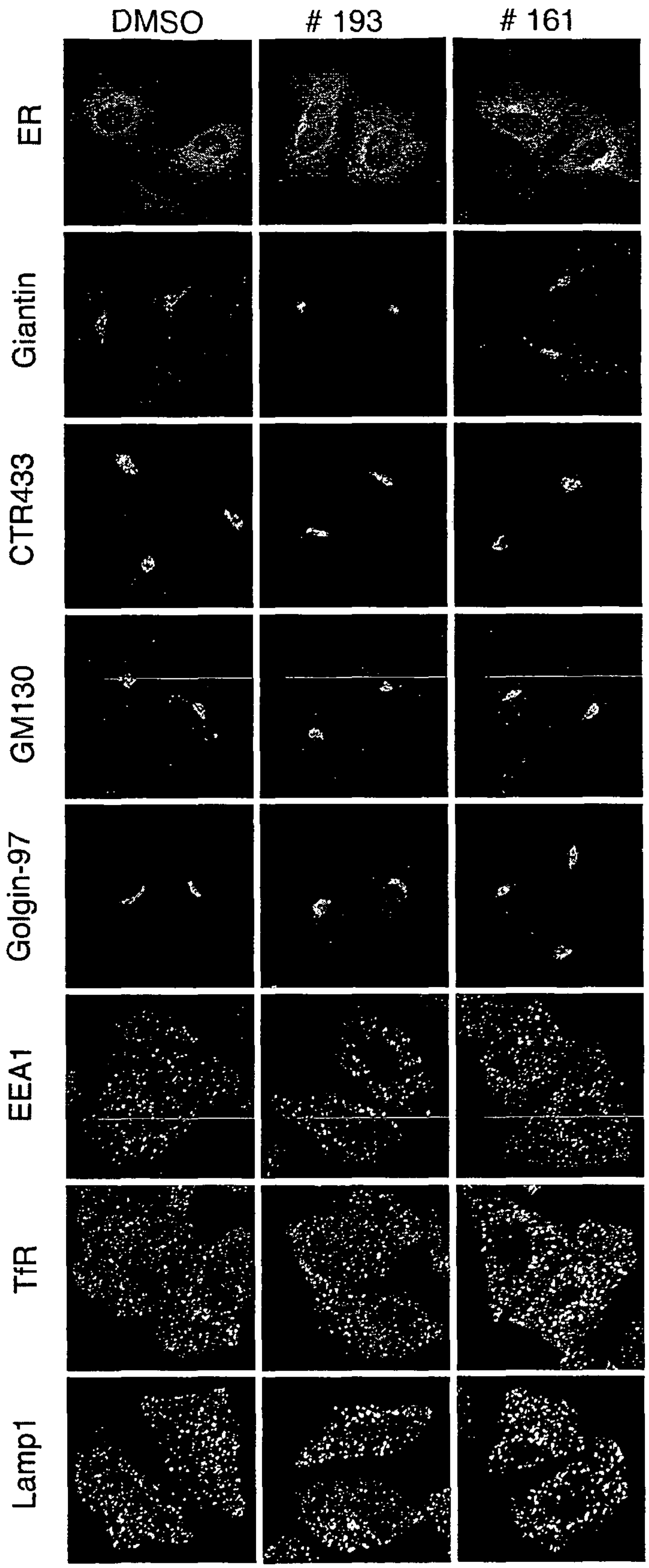
FIG. 5 shows pictures of cells structures after incubation with compounds 161 and 193.

No difference between control and compound-treated cells could be observed. Also, the overall organelles and cellular morphologies were unaltered (FIG. 5). Thus, the inhibition of Stxs trafficking by Compounds 161 and 193 is most likely not due to any unspecific, general effect on the cellular integrity as seen for other inhibitors of the retrograde route.

6. Effects of Compounds 161 and 193 on Lysosomal Degradation

In order to determine the effect of the compounds on the degradation of endocytosed cargos along the degradative (lysosomal) pathway, $^{125}$I-EGF was used as a tracer. HeLa-cells were pre-treated with the compounds 161 and 193, prior to incubation with $^{125}$I-EGF on ice for 30 min. After several washing steps, the cells were shifted to 37° C. in the presence of compounds. The radioactivity in TCA-insoluble and TCA-soluble fractions was quantified by scintillation after various time-points between 0-240 min.

Figure 6:
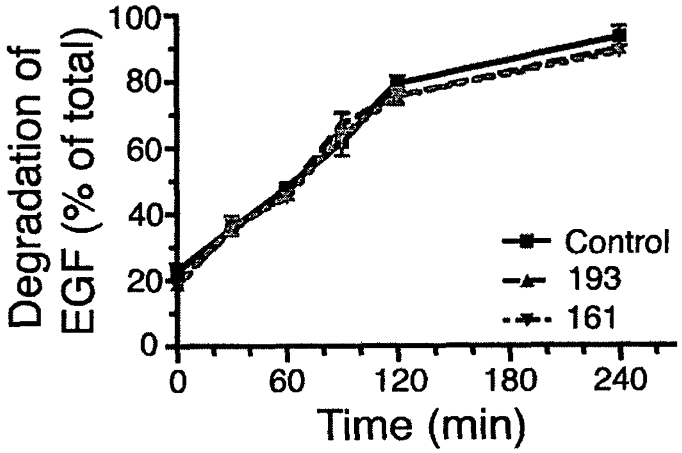
FIG. 6 is a graph representing the degradation of EGF with or without compounds 161 or 193; EGF degradation being a tracer of lysosomal degradation.

Data from control and compound-treated cells were identical, suggesting that compounds 161 and 193 have no effect on lysosomal degradation (FIG. 6).

7. Effects of Compounds 161 and 193 on the Anterograde (Secretory) Pathway

The effect of compounds 161 and 193 was quantitatively determined by measuring the secretion of vesicular stomatitis virus G protein (VSVG) in control and inhibitors-treated cells (Amessou et al (2007) J Cell Sci 120, 1457-1468). Cells were transfected with GFP-VSVG$^{ts045}$ and incubated overnight at 40° C. Under these conditions, the protein accumulates in the endoplasmic reticulum. Transport to the Golgi complex and plasma membrane is initiated by shifting cells to 32° C., and expression at the plasma membrane is quantified by FACS using an anti-VSVG antibody.

Figure 7:
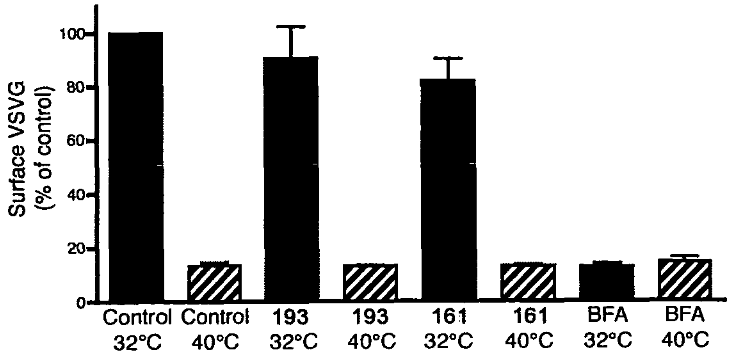
FIG. 7 is a graph showing the GFP-VSVG$^{ts045}$-secretion by transfected HeLa cells in the absence and presence of compound 193, compound 161 and brefeldin A (BFA).

The anterograde transport of GFP-VSVG$^{ts045}$ was not significantly reduced upon treatment with compounds 161 and 193 in contrast to brefeldin A. The results show that compound 161 and 193 block the retrograde pathway only but not the anterograde secretion route (FIG. 7).

8. Toxin Binding on Cells

The amount of bound StxB on cells was not reduced by compound 161 or 193, as quantified by FACS.

HeLa-cells were compound-treated (30 min, 37° C., 20 μM), incubated on ice with STxB-Cy5 (1 μM) for 30 min, washed three times in 3% FCS/PBS, and analyzed by FACS (FACSCalibur). The fluorescence intensity corresponds to bound STxB-Cy5 on HeLa cells. 20.000 cells were analyzed for each condition. As a negative control, Gb3-depleted HeLa cells were used. For this, HeLa-cells were treated for 6 days with 5 μM of the glucosylceramide synthase inhibitor 1-phenyl-2-hexadecanoyl-amino-3-morpholino-1-propanol (PPMP).

9. Toxin Uptake in Presence of Compounds 161 and 193

Figure 8:
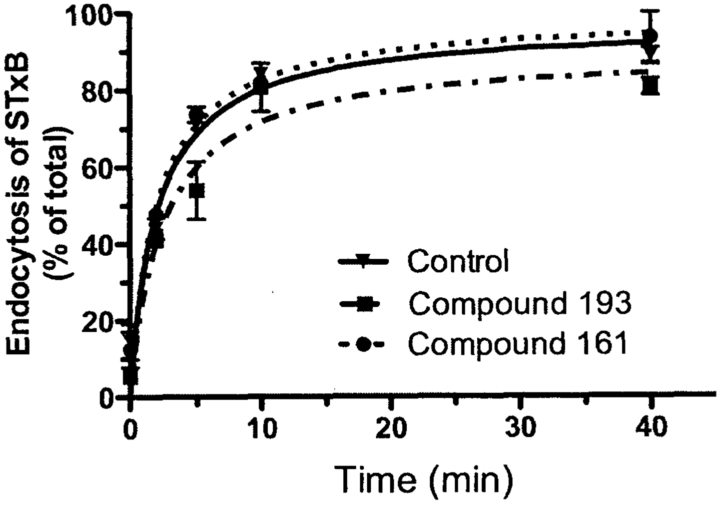
FIG. 8 is a graph showing the Shiga toxin uptake in absence (control) and presence of compound 161 or compound 193.
Figure 9:
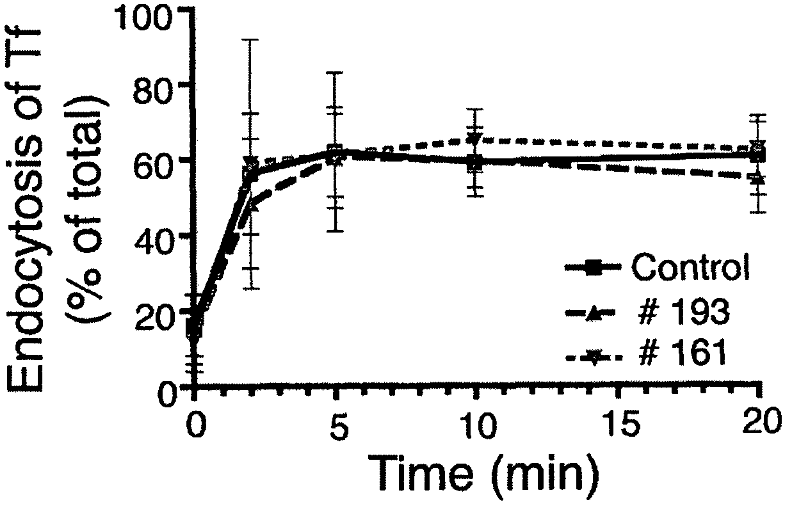
FIG. 9 is a graph showing the transferrin (Tf) uptake in absence (control) and presence of compound 161 or compound 193.

The endocytosis of StxB and transferrin (Tf) was not altered after the treatment with both compounds 161 or 193. For demonstrating this, cells were compound-treated (20 μM, 30 min, 37° C.), incubated on ice with StxB or Tf that are linked via a reducible disulfide bond to biotin (StxB-SS-Biotin and Tf-SS-Biotin). After washing, cells are incubated at 37° C. for different times. Biotin on surface-exposed STxB-SS-Biotin or Tf-SS-Biotin was cleaved by subsequent treatment with the non-membrane-permeable reducing agent MESNA (2-mercaptoethansulfonic acid). Under these conditions, internalized StxB-SS-Biotin and Tf-SS-Biotin are protected from the reduction. After inactivation of MESNA by addition of iodoacetamide (150 mM) and cell lysis, biotinylated STxB and Tf were quantified by ELISA using anti-STxB mAb 13C4, anti-Tf mAb H68.4 and streptavidin-HRP StxB and Tf are similarly internalized into control and compound-treated cells (FIGS. 8 and 9).

10. Effect of Compounds 161 and 193 on Retrograde Transport of Endogenous Cargos (TGN46, CI-M6PR)

Figure 10:
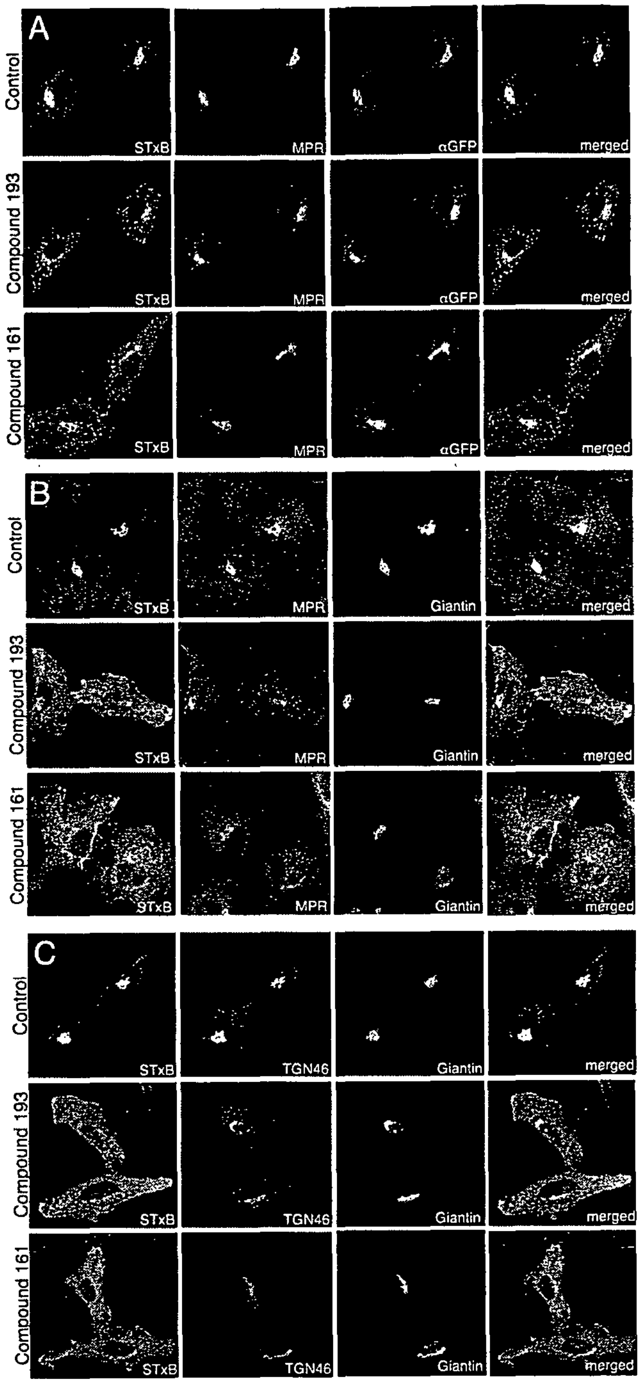
FIG. 10 is a graph showing the absence of effects of compounds 161 and 193 on cellular transport of endogenous cargos MPR and TGN46 (legend: (A) MPR-uptake on HeLa-MPR, (B and C) Steady-state localization of TGN46 and CI-MPR).

To characterize the inhibitory effect of compounds on endogenous cargos, the transport of either CI-M6PR or TGN46 was compared between compound-treated and control cells. HeLa-cells over-expressing MPR-GFP were pretreated with 20 μM of compounds 193 or 161 for 30 min at 37° C. (FIG. 10A). After binding of STxB-Cy3, cells were incubated with anti-GFP antibody for 40 min at 37° C. During this time, the antibody binds to cell-surface MPR-GFP, and the MPR-GFP/anti-GFP antibody-complex is internalized and transported to the Golgi apparatus, where it colocalizes with Giantin, a Golgi-marker. Note, that in compound-treated cells, where the retrograde transport of STxB to the TGN is inhibited, the MPR-GFP/anti-GFP antibody-complex is still transported efficiently to the Golgi, suggesting that the two compounds are cargo-specific (i.e. no effect on MPR-transport).

HeLa-cells were treated for 5.5 h at 37° C. with 20 μM of compounds 193 or 161 (FIGS. 10B and 10C). After binding of STxB-Cy3 on ice, cells were incubated for another 45 min at 37° C. in the presence of compounds 193 or 161, fixed and stained for the indicated antibodies. Note that the steady-state localization of CI-MPR and TGN46 is similar under control and compound-treatment conditions. These results suggest, that both compounds have no effect on the transport of both proteins, and thus on their steady-state localization.

It has not been observed a distinct inhibition of the transport of CI-M6PR and TGN46 induced by either compounds 161 or 193, further substantiating the specificity of both compounds towards exogenous toxins. This finding is highly surprising as to date all trafficking factors that have been found to be required for Shiga toxin transport have also been shown to be required for mannose 6-phosphate transport, when this was directly tested (Amessou et al., 2007). The finding that compounds 161 and 193 inhibit Shiga toxin trafficking without affecting mannose 6-phosphate transport is therefore highly unexpected.

11. Compounds 161 and 193 Effects are Robust and Observed on Others Human Cell Lines Besides HeLa-cells, human monocytic, Gb3-expressing THP1-cells were used to characterize the inhibitory effect of the compounds. Concentrations of up to 100 μM of compounds did not cause any reduction in the overall protein biosynthesis. By using immunofluorescence, THP1-cells were incubated with 100 μM of compound for 30 min at 37° C., before binding of StxB on ice for 30 min and internalization for 45 mn at 37° C. Fixed cells were stained for the Golgi-marker giantin.

In line with the effect observed on HeLa-cells, a stark reduction of retrograde transport of StxB to the TGN was observed on THP1-cells treated with compounds 161 or 193. This suggests that the effect of these compounds is not restricted to a single cell-line, but can be observed on cells as diverse as epithelial HeLa-cells and monocytic THP1-cells.

CONCLUSION

In the case of Stxs, after treatment with compounds 161 or 193 of toxin-sensitive HeLa-cells, a 50-100× higher dose of toxin is necessary to cause a similar inhibitory effect on protein-biosynthesis as on control cells. This effect is attributed to an inhibition in the retrograde transport of the toxin at the interface between early endosomes and Golgi apparatus, and it is not due to a reduction in toxin binding or internalization, or an unspecific effect on cellular morphology or functional alteration of cellular compartments. The transport of StxB to the trans-Golgi network was reduced by 60-90%, as verified by sulfation assay. Compound-treatment of cells leads to an accumulation of StxB and CtxB in early endosomes. The effect of these compounds is confined to retrograde transport and does not affect other transport pathways, e.g. anterograde (secretory) or late endosomal (degradative) pathway. Even though these compounds impair the transport of exogenous toxins, Inventors unexpectedly did not observe a pronounced effect on endogenous cargos, such as CI-M6PR (cation-independent mannose-6-phosphate receptor) or TGN46. Long-term treatment up to 3 days does not reduce cellular growth. On THP-1-cells, compounds 161 and 193 concentrations as high as 100 μM did not cause any apparent side effects.

In contrast to others small molecules, compounds 161 and 193 are specific to exogenous toxins (Shiga and cholera toxins) and they unexpectedly do not impact distinctly the transport of endogenous cargo (CI-M6PR, TGN46). Additionally, these compounds do no have any effect on the morphology of cellular compartments and do not influence cellular growth even after longer treatments (several days). Also, their effect is restricted to the retrograde transport route and does not influence anterograde transport, degradation or endocytosis.

The invention claimed is:

1. A method for treating a disorder caused by a Shiga toxin or a related toxin, the method comprising administering to a subject in need thereof an effective amount of an imine derivative compound of the formula (I):

(I)

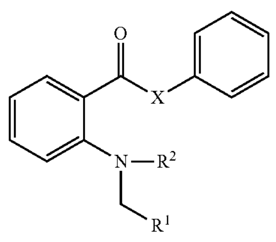

, wherein:

X is —NH— or —O—;

$R^1$ is a cycloalkyl radical having 5 to 10 carbon atoms, having one or two rings, saturated or not, wherein one or more carbon atoms are optionally replaced by a nitrogen, oxygen or sulfur atom, and wherein said cycloalkyl radical is optionally substituted by at least one substituent selected from the group consisting of a halogen atom, a hydroxyl function, a nitro function, and a $C_1$-$C_3$ alkyl group; and $R^2$ is a hydrogen atom or a link, and when $R^2$ is a link, the nitrogen atom to which $R^2$ is bonded forms a double bond with the adjacent non-aromatic carbon atom.

2. The method according to claim 1, wherein the compound of the formula (I) is at least one selected from the group consisting of:

2-(3-bromobenzylideneamino)-N-phenylbenzamide;
2-(3-bromobenzylamino)-N-phenylbenzamide;
2-(3-fluorobenzylideneamino)-N-phenylbenzamide;
(E)-2-((furan-2-yl)methyleneamino)-N-phenylbenzamide;
(E)-2-((furan-3-yl)methyleneamino)-N-phenylbenzamide;
(E)-2-((5-methylfuran-2-yl)methyleneamino)-N-phenylbenzamide;
(E)-2-(5-fluoro-2-nitrobenzylideneamino)-N-phenylbenzamide;
(E)-2-(4-fluorobenzylideneamino)-N-phenylbenzamide;
(E)-2-(2-fluorobenzylideneamino)-N-phenylbenzamide;
(E)-2-((1-methyl-1-indol-2-yl)methyleneamino)-N-phenylbenzamide;
(E)-2-(5-bromo-2-hydroxybenzylideneamino)-N-phenylbenzamide;
2-(2-fluorobenzylamino)-N-phenylbenzamide; and
(E)-2-(2-(5-methylthiophen-2-yl)vinyl)-N-phenylbenzamide.

3. The method according to claim 1, wherein the Shiga toxin or related toxin comprises:

the Shiga toxin (Stx) produced by *Shigella dysenteriae;*

Shiga-like toxin 1 and 2, which is SLT-1 and 2 or Stx-1 and 2 or Verotoxin 1 and Verotoxin 2, produced by Shiga-toxigenic group of *Escherichia coli* (STEC); or cholera toxin (Ctx).

4. The method according to claim 1, wherein the disorder is at least one selected from the group consisting of abdominal pain, nausea, vomiting, diarrhea, watery diarrhea, bloody diarrhea, a complication of hemolytic uremic syndrome (HUS) selected from the group consisting of microangiocytopenia anemia, thrombocytopenia, and nephropathy, and an extra-renal complication of HUS selected from the group consisting of seizure, intracranial infarction, intracranial hemorrhage, retinal hemorrhage, retinal encephalopathy, acute pancreatitis, and cardiomyopathy.

* * * * *